US00RE41467E

(19) United States
(12) Reissued Patent
Saito et al.

(10) Patent Number: US RE41,467 E
(45) Date of Reissued Patent: *Aug. 3, 2010

(54) ENDOSCOPIC IMAGING SYSTEM IN WHICH STILL IMAGE-SPECIFIC OR MOTION PICTURE-SPECIFIC EXPANSION UNIT CAN BE COUPLED TO DIGITAL VIDEO OUTPUT TERMINAL IN FREELY UNCOUPLED MANNER

(75) Inventors: Katsuyuki Saito, Sagamihara (JP); Akihiko Mochida, Hino (JP); Kotaro Ogasawara, Tokyo (JP); Noboru Kusamura, Hachioji (JP); Makoto Tsunakawa, Chofu (JP); Hideki Tashiro, Yokohama (JP); Shinji Yamashita, Fuchu (JP); Kanichi Matsumoto, Hino (JP); Wataru Ohno, Sagamihara (JP); Masahiro Hagihara, Hachioji (JP); Kazutaka Nakatsuchi, Hino (JP); Kuniaki Kami, Machida (JP)

(73) Assignee: Olympus Corporation (JP)

( * ) Notice: This patent is subject to a terminal disclaimer.

(21) Appl. No.: 10/144,381

(22) Filed: May 9, 2002

Related U.S. Patent Documents

Reissue of:
(64) Patent No.: 6,184,922
Issued: Feb. 6, 2001
Appl. No.: 09/126,249
Filed: Jul. 30, 1998

(30) Foreign Application Priority Data

Jul. 31, 1997 (JP) ..... H9-206678
Aug. 1, 1997 (JP) ..... H9-208122

(51) Int. Cl.
*A62B 1/04* (2006.01)

(52) U.S. Cl. ..... 348/65; 348/75; 600/109

(58) Field of Classification Search ..... 348/65, 348/68–69, 72, 75, E5.044, 73; 600/109–112, 600/101, 104, 122, 123; 128/4; *H04N 1/64*
See application file for complete search history.

(56) References Cited

U.S. PATENT DOCUMENTS

| | | | |
|---|---|---|---|
| 4,727,417 | A | 2/1988 | Kanno et al. |
| 5,124,789 | A | 6/1992 | Hiyama et al. |
| 5,592,216 | A | 1/1997 | Uehara et al. |
| 5,697,885 | A | 12/1997 | Konomura et al. |
| 5,801,762 | A | 9/1998 | Dianna et al. |
| 5,980,450 | A | 11/1999 | Thompson |
| 5,993,381 | A | 11/1999 | Ito |

*Primary Examiner*—Nhon T Diep
(74) *Attorney, Agent, or Firm*—Ostrolenk Faber LLP

(57) ABSTRACT

A camera control unit for processing a signal output from an imaging device incorporated in an endoscope is provided with an analog video signal output terminal through which a video signal is output to a monitor, and a digital video signal output terminal to which a still image-specific or motion picture-specific expansion unit is coupled in a freely detachable manner. By handling a release switch, a still image or motion picture can be recorded digitally. Even when the recorded image data is edited or subjected to any other processing, deterioration of image quality can be prevented. An imaging system having these advantages can be realized on a small scale.

52 Claims, 15 Drawing Sheets

ENDOSCOPIC IMAGING SYSTEM IN WHICH STILL IMAGE-SPECIFIC OR MOTION PICTURE-SPECIFIC EXPANSION UNIT CAN BE COUPLED TO DIGITAL VIDEO OUTPUT TERMINAL IN FREELY UNCOUPLED MANNER

Matter enclosed in heavy brackets [ ] appears in the original patent but forms no part of this reissue specification; matter printed in italics indicates the additions made by reissue.

BACKGROUND OF THE INVENTION

1. Field of the Invention

The present invention relates to an endoscopic imaging system in which a still image-specific or motion picture-specific expansion unit can be coupled in a freely detachable manner to a digital video output terminal of a camera control unit for processing a signal sent from an imaging device incorporated in an endoscope.

2. Description of the Related Art

In recent years, endoscopes have been widely adopted in the fields of medicine and industries alike. Moreover, an endoscopic imaging system has come to be adopted widely. In the endoscopic imaging system, a TV camera-mounted endoscope having a TV camera which includes an imaging means mounted on an eyepiece unit of an optical endoscope, or an electronic endoscope including an imaging means in a distal part thereof is used to produce an endoscopic image, and the endoscopic image is displayed on a monitor.

Assume that such an endoscopic imaging system is used, for example, to conduct an endoscopic examination in the field of medicine. In this case, an operator often records images (photographs an object) using a photography unit or produces hard copies of endoscopic images by outputting image data to a video printer so that he/she can utilize them for future diagnosis.

Moreover, image data may be output to an image filing system for recording of endoscopic images.

Moreover, a video tape recorder (VTR) has been adopted for recording a motion picture.

However, when the photography unit is employed, it takes much time to complete development of a film. In addition, a request for checking an image right away cannot be met, as is possible when the video printer is employed. However, as far as the photography unit or video printer is concerned, management of developed films or print sheets is a nuisance. Since it is hard to retrieve the films or print sheets, the films or print sheets are usually manually filed. This brings about a drawback that the filing (using an image scanner) is time-consuming.

Moreover, when an image filing system is employed, image retrieval can be achieved readily. However, a system including the image filing system becomes large in scale. Such a system can be installed only in a hospital that is somewhat large in scale. Furthermore, a location in which such retrieval is carried out is restricted.

Moreover, in some clinical cases, image data of a motion picture is recorded. However, there is a drawback that when the VTR is used to dub films or to edit or manipulate the image data, image quality deteriorates.

SUMMARY OF THE INVENTION

An object of the present invention is to provide an endoscopic imaging system making it possible to readily retrieve or edit image data of even a still image or a motion picture, and to suppress deterioration of image quality.

Another object of the present invention is to provide an endoscopic imaging system designed compactly and capable of providing endoscopic image data that can be readily retrieved or edited.

Still another object of the present invention is to provide an endoscopic imaging system including a simply structured external storage and capable of readily fetching digital image data.

An endoscopic imaging system of the present invention comprises:

- an endoscope including an illumination optical system located at and end of an elongated insertion unit for emitting illumination light, an objective optical system located at the distal end of the insertion unit for forming an optical image of an object illuminated with the illumination light, and an imaging device for photoelectrically converting the optical image directly or the optical image that has been transmitted through the insertion unit;
- a signal processing apparatus for driving the imaging device, processing an image signal output from the imaging device, producing digital and analog video signals, and outputting the digital and analog video signals through a digital video signal output terminal and analog video signal output terminal, respectively;
- a monitor for displaying an object image represented by the analog video signal in response to an input of the analog video signal output through the analog video signal output terminal; and
- an expansion unit to be coupled to the digital video signal output terminal in a freely detachable manner, and including at least one of a compression unit for compressing the digital video signal and a PC card slot to which a PC card, in which a motion picture digital video signal representing a motion picture whose data has been compressed by the compression unit and a digital video signal representing a still image whose data has been compressed by the compression unit are stored, can be coupled in the freely detachable manner.

An operator should merely connect an expansion unit specific to still images or motion pictures according to the kind of image to be recorded. Thus, image data can be compressed and recorded digitally. Retrieval, editing, and manipulation of the image data can therefore be carried out easily. Even if manipulation or the like is repeated, resultant deterioration of image quality can be minimized.

BRIEF DESCRIPTION OF THE DRAWINGS

FIGS. 1 to 8B relate to a first embodiment of the present invention;

FIG. 1 is an oblique view showing a configuration of an endoscopic imaging system of the first embodiment;

FIG. 2 is a block diagram showing an internal configuration of a CCU and the like;

FIG. 3 is a block diagram showing a configuration of a still image-specific expansion unit;

FIG. 5 is a block diagram showing a configuration of a compression circuit specific to motion pictures;

FIGS. 8A and 8B are diagrams showing examples of use of small memory cards for explaining the operations thereof;

FIG. 14 is a diagram showing a configuration of an endoscopic imaging system of the sixth embodiment;

FIG. 15 is a diagram showing a configuration of a digital interface unit shown in FIG. 1;

FIG. 16 is a timing chart of a digital video signal to be input to the digital interface unit shown in FIG. 2;

FIG. 17 is a diagram showing an example of extracting a clock signal (CLK) from a horizontal synchronizing signal (H-SYNC) shown in FIG. 16;

DESCRIPTION OF THE PREFERRED EMBODIMENTS

The first embodiment of the present invention will be described with reference to FIGS. 1 to 8.

Figure 1:
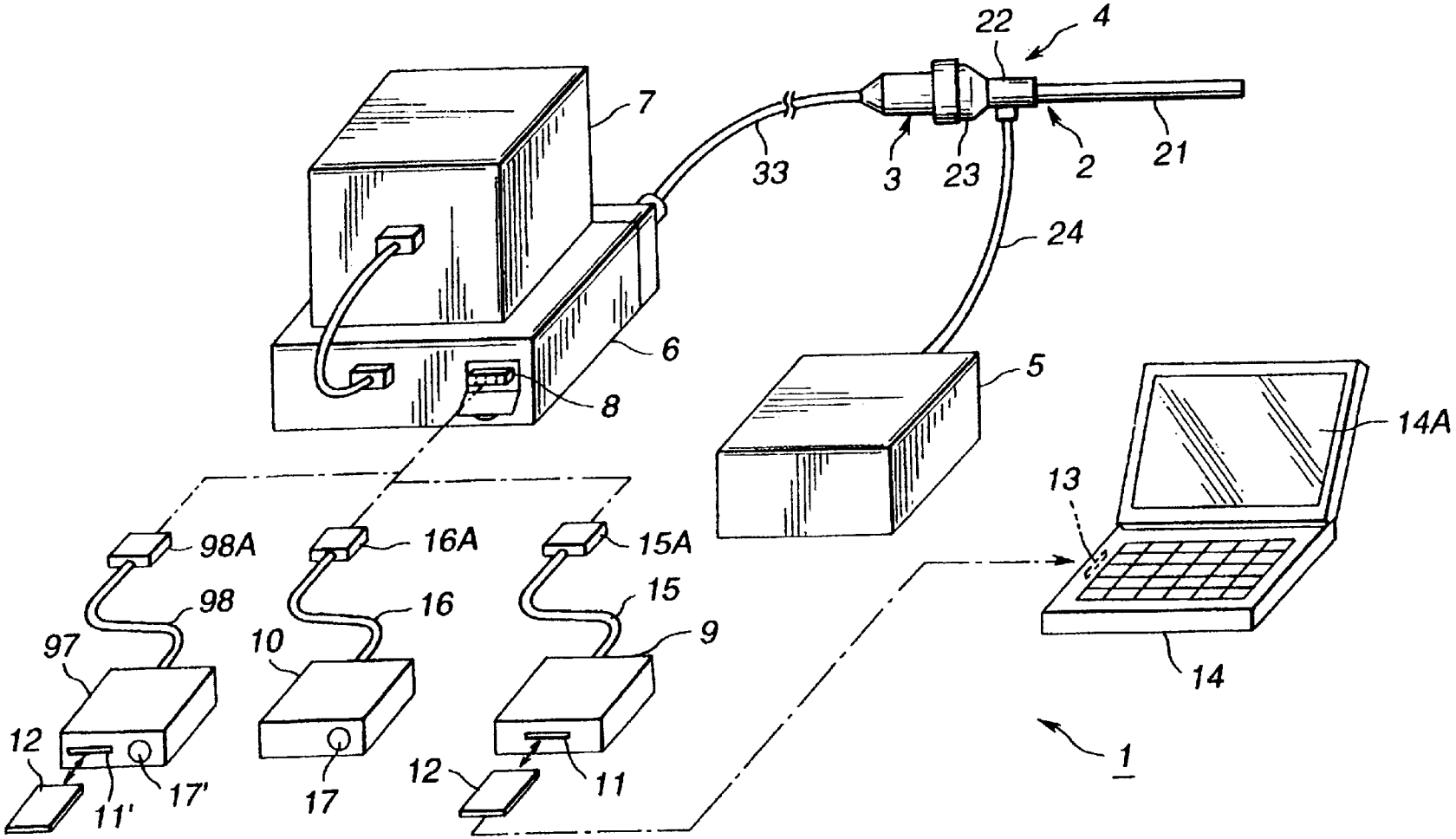

As shown in FIG. 1, an endoscopic imaging system 1 of the first embodiment of the present invention comprises: a TV camera-mounted endoscope 4 having a TV camera 3 mounted on a rigid endoscope 2; a light source apparatus 5 for supplying illumination light to the rigid endoscope 2; a camera control unit (hereinafter a CCU) 6 serving as an endoscopic imaging apparatus for processing a signal sent from an imaging means in the TV camera 3; a color monitor 7 for displaying an image represented by a video signal output from the CCU 6; a still image-specific expansion unit 9 and motion picture-specific expansion unit 10 selectively coupled to a digital video output terminal 8 of the CCU 6 through which a digital video signal is output so that the selected expansion unit can be uncoupled freely; and a personal computer 14 having a PC card slot 13 to which a PC card 12, such as a flash memory card, which can be coupled to a PC card slot 11 of the still image-specific expansion unit 9 in a freely detachable manner, is coupled in the freely detachable manner.

What is referred to as a PC card is peripheral equipment sized like a credit card in conformity with the PC Card Standard. The PC card was standardized by the Personal Computer Memory Card International Association and the Japan Electric Industry Development Association in 1995.

The still image-specific expansion unit 9 and motion picture-specific expansion unit 10 are provided with cables 15 and 16, respectively, having connectors 15A and 16A, respectively, spliced to one end thereof. The connectors 15A and 16A are coupled to a digital video output terminal 8 of the CCU 6 so that they can be uncoupled freely. One of the still image-specific expansion unit 9 and motion picture-specific expansion unit 10 can be selected and connected to the CCU 6.

Alternatively, a still image & motion picture-specific expansion unit 97 can be selectively connected to the CCU 6. The still image & motion picture-specific expansion unit 97 is a unit into which the still image-specific expansion unit 9 and motion picture-specific expansion unit 10 are integrated (that is, having the ability to compress still-image data and record resultant data on a PC card 12 that is loaded into a PC card slot 11', and also having the ability to compress motion-picture data and output resultant data through a digital video output terminal 17'). The still image & motion picture-specific expansion unit 97 is also provided with a cable 98 having a connector 98A spliced to an end thereof. The connector 98A is coupled to the digital video output terminal 8 of the CCU 6 so that it can be uncoupled freely.

Moreover, the still image-specific expansion unit 9 and motion picture-specific expansion unit 10 are provided with the PC card slot 11 and digital video output terminal 17, respectively. The PC card 12 is loaded into the PC card slot 11 so that it can be unloaded freely. Still-image data compressed by a still image compressing means incorporated in the still image-specific expansion unit 9 can be recorded on the PC card 12.

Moreover, a digital video disk (DVD) drive (DVD-RAM drive or DVD-R drive), not shown, having a recording facility may be connected to the motion picture-specific expansion unit 10 through the digital video output terminal 17 through which compressed motion-picture data is output. In this case, motion-picture data compressed by a motion picture compressing means incorporated in the motion picture-specific expansion unit 10 can be recorded.

Moreover, the data may be input to the personal computer 14 and edited.

The rigid endoscope 2 includes an elongated insertion unit 21, a hand-held unit 22 formed at the back end of the insertion unit 21, and an eyepiece unit 23 formed at the back end of the hand-held unit 22. The hand-held unit 22 has a light guide base and is connected to the light source apparatus 5 over a light guide cable 24.

Figure 2:
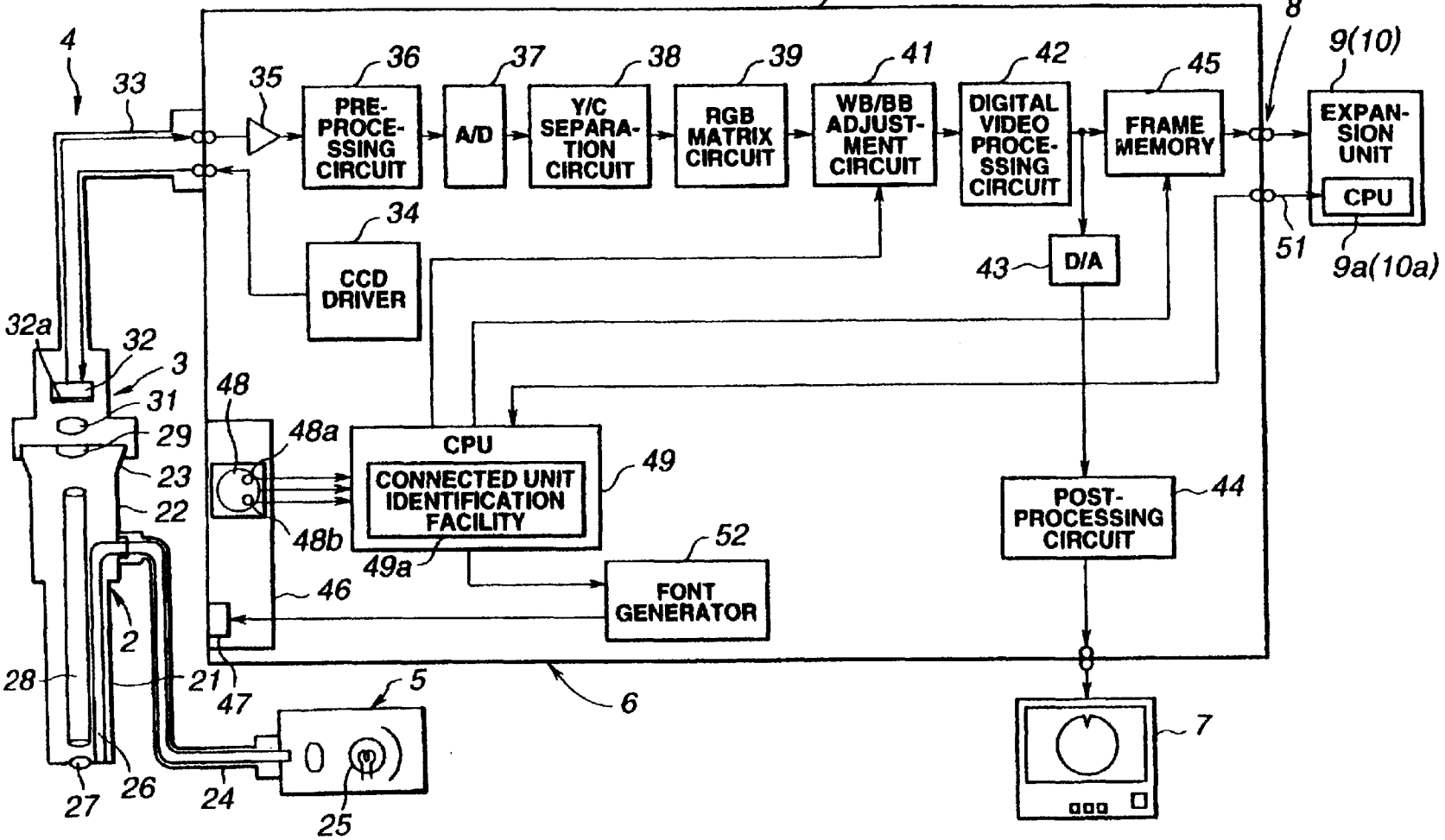

As shown in FIG. 2, white illumination light emanating from a lamp 25 in the light source apparatus 5 is converged by a condenser and supplied to a light guide in the light guide cable 24. The illumination light is propagated through a light guide 26 in the rigid endoscope 2, and emitted forward through the distal end of the light guide fitted in an illumination window in the distal part of the insertion unit 21. An object such as a lesion is thus illuminated.

An objective lens 27 is fitted in an observation window adjacent lens to the illumination window. The objective forms an object image at the image formation position thereof. The formed image is transmitted by a system of relay lenses 28 arranged in the insertion unit 21 and opposed to the objective lens 27. The system of relay lenses forms an image near the eyepiece unit 23. The image is re-formed on a solid-state imaging device or specifically a charge-coupled device (hereinafter a CCD) 32 by means of an eyepiece 29 included in the eyepiece unit 23 and an image formation lens 31 in the TV camera 3 which is opposed to the eyepiece 29.

A mosaic filter 32a is placed in front of the image plane (photoelectric conversion plane) of the CCD 32. Color components of light input to each pixel are optically separated from one another. This means that the imaging means of this embodiment is a simultaneous imaging means for producing a color image signal under white-light illumination.

The CCD 32 is connected to the CCU 6 over a camera cable 33. With application of a CCD driving signal from a CCD driver 34 in the CCU 6 to the CCD 32, a CCD output signal (image signal) photoelectrically converted and output by the CCD 32 is input to a preamplifier 35 in the CCU 6. The signal amplified by the preamplifier 35 is then input to the pre-processing circuit 36.

The CCD output signal input to the pre-processing circuit 36 is pre-processed by performing correlation double sampling (CDS) or sample-and-hold (S/H). A resultant signal is input to an A/D converter 37 and converted into a digital signal. The digital signal is input to a Y/C separation circuit 38.

The digital signal input to the Y/C separation circuit 38 is recomposed according to the line-sequential color imaging. Digital signals Y, Cr, and Cb of three channels are then separated from one another, and input to an RGB matrix circuit 39.

The digital signals Y, Cr, and Cb input to the RGB matrix circuit 39 are converted into a digital signal RGB according to the matrix algebra.

On the succeeding side of the RGB matrix circuit 39, there is a white balance/black balance (abbreviated to WB/BB in FIG. 2) adjustment circuit 41. The digital signal RGB converted according to the matrix algebra is input to the white balance/black balance adjustment circuit 41. After the signal undergoes the given balance adjustment, it is input to a digital video processing circuit 42.

The digital video processing circuit 42 carries out digital processing such as enhancement, gamma correction, and character convolution. A resultant signal is input to a D/A converter 43. The digital signal input to the D/A converter 43 is converted into an analog signal, and then converted into a standard video signal by a post-processing circuit 44. The standard video signal is output to a color monitor 7 through an analog video output terminal.

Moreover, an output of the digital video processing circuit 42 is stored temporarily in a frame memory 45. The digital video signal stored in the frame memory 45 is output to the expansion unit 9 or 10 coupled to the digital video output terminal 8 through the digital video output terminal 8.

Moreover, for example, a front panel 46 of the CCU 6 is provided with a display LED 47 for indicating the number of frames of a still image to be recorded or a recording time of a motion picture, and a release switch 48. The release switch 48 is connected to the CPU 49. A release instruction signal generated by handling the release switch 48 is transmitted to the CPU 49.

In response to the release instruction signal, the CPU 49 sends a release signal to a control means (for example, a CPU 9a (10a) in the expansion unit 9 or 10 through a communication line 51 over which a control signal is transmitted.

Incidentally, the CPU 49 has a facility for recognizing whether an expansion unit coupled to the digital video output terminal 8 is the still image-specific expansion unit 9 or the motion picture-specific expansion unit 10, i.e., a connected unit identification facility 49a.

For example, the control means in the expansion unit 9 or 10 is instructed to send a unit identification signal used to identify the expansion unit 9 or 10 over the communication line 51. The control means in the expansion unit 9 or 10 returns a unit identification signal over the communication line 51. Based on the unit identification signal, a connected expansion unit is recognized as the still image-specific expansion unit 9 or motion picture-specific expansion unit 10. When the still image & motion picture-specific expansion unit 97 is connected, a unit identification signal associated with the still image & motion picture-specific expansion unit 97 is returned to the CPU 49.

Alternatively, instead of employing the foregoing identification means, different resistors or the like may be connected to the contact pins of the connectors 15A and 16A. In this case, when the connector 15A or 16A is coupled to the digital video output terminal 8 of the CCU 6, the resistances of the resistors are checked. Thus, a connected expansion unit is recognized as the still image-specific expansion unit 9 or motion picture-specific expansion unit 10.

The CPU 49 has the facility for identifying an expansion unit coupled to the digital video output terminal 8 as the still image-specific expansion unit 9 or the motion picture-specific expansion unit 10. When the release switch 48 is handled, the CPU 49 carries out an associated control operation.

When a unit coupled to the digital video output terminal 8 is the still image-specific expansion unit 9, the release signal is sent to CPU 49, whereupon image data of a still image is stored in the frame memory 45 (writing is inhibited). The still image-specific expansion unit 9 carries out releasing, that is, compresses image data of a still image input through the digital video output terminal 8 and records the image data on the PC card 12 loaded into the PC card slot 11. Thereafter, the control means in the still image-specific expansion unit 9 reports the fact that data of a still image of one frame has been recorded to the CPU 49 over the communication line 51.

The CPU 49 uses a font generator 52 to control display of the display LED 47 so that the number of frames set before the release switch 48 is handled will be incremented by one and displayed.

Moreover, assume that a unit coupled to the digital video output terminal 8 is the motion picture-specific expansion unit 10. When the release signal is received, image data of a motion picture input from the frame memory 45 through the digital video output terminal 8 is compressed. The release signal is sent to peripheral equipment such as a DVD coupled to the digital video output terminal 17 through the digital video output terminal 17. The peripheral equipment carries out the process of starting a recording of compressed image data. The peripheral equipment then sends a signal indicating that recording has been started to the CPU 49 over the communication line 51.

The CPU 49 then displays a message saying that recording of a motion picture has started (for example, a message of "Picture recording"). The CPU 49 controls the display LED 47 via the font generator 52 so that the display LED 47 will display a recording time having elapsed since a recording start time instant 0.

Incidentally, when the motion picture-specific expansion unit 10 is connected, the CPU 49 updates (writes or reads)

image data existent in the frame memory 45 at intervals of a certain time frame.

As mentioned above, when the CPU 49 receives the release instruction signal, it sends a release signal to the expansion unit 9 or 10 over the communication line 51 so that image data will be fetched from the frame memory 45 and recorded. The expansion unit 9 or 10 reports the fact that releasing has been carried out to the CPU 49 over the communication line 51. The CPU 49 displays the number of received frames or the like on the display LED 47.

When the release switch 48 is pressed, a still image or motion picture is recorded automatically according to the result of the automatic identification performed by the connected unit identification facility 49a, that is, according to whether a connected expansion unit is the still image-specific expansion unit 9 or the motion picture-specific expansion unit 10. Alternatively, automatic identification may be omitted. Instead, a still image-specific release switch 48a or a motion picture-specific release switch 48b, which is part of the large release switch 49, may be handled in order to given an instruction for recording a still image or motion picture. In particular, when the still image & motion picture-specific expansion unit 97 is connected, the still image-specific release switch 48a or motion picture-specified release switch 48b should be employed.

Incidentally, the CPU 49 controls the operations performed by the white balance/black balance adjustment circuit 41 and the read or write operation relative to the frame memory 45.

Figure 3:
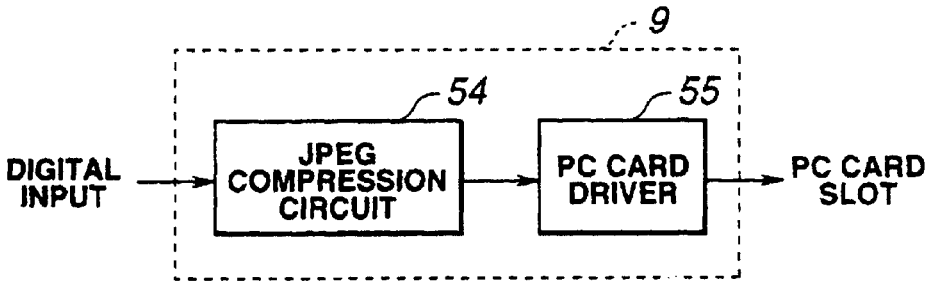

As shown in FIG. 3, the still image-specific expansion unit 9 consists of a JPEG (Joint Photographic Coding Group) compression circuit 54 and a PC card driver 55. The JPEG compression circuit 54 falls into either a lossless coding type of compressing data of a color still image according to the lossless coding and a lossy coding type of compressing it according to the lossy coding.

As far as data compressed according to the lossless coding is concerned, decompression can restore it to its original information quality. By contrast, data compressed according to the lossy coding cannot be fully restored to its original information quality.

The spatial predictive coding is adopted as the former lossless coding. In this case, the level of compressibility is lower than that permitted by the lossy coding. However, since original image quality can be retained, if deterioration of image quality cannot be accepted, this coding would be effective.

On the other hand, the DCT (discrete cosine transform) coding is a baseline of the lossy coding. Although an original image cannot be reproduced exactly, decoded data representing an image of quality that is good enough for practical use can be produced.

Figure 4A:
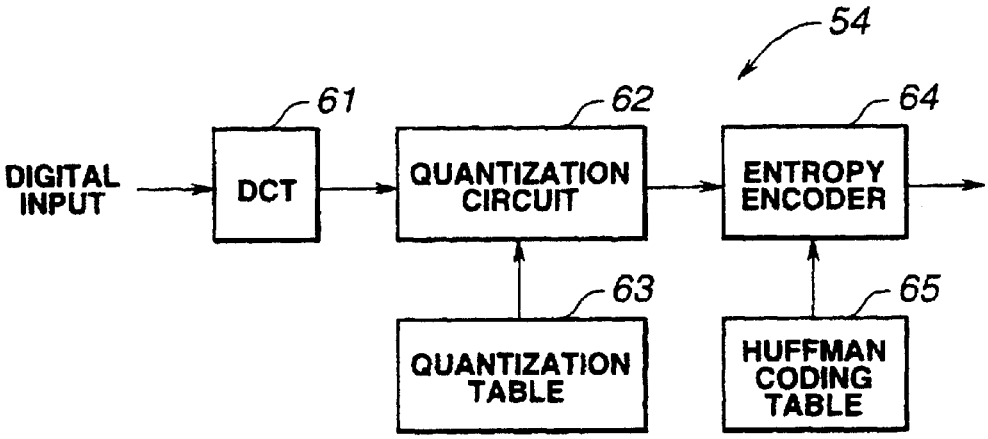
FIGS. 4A and 4B are block diagrams showing configurations of JPEG compression circuits of the lossy and lossless coding types.

FIG. 4A shows a configuration of the JPEG compression circuit 54 adopting the DCT coding which is employed in this embodiment. As shown in FIG. 4A, digital image data is input to a DCT circuit 61 in units of a block of 8 by 8 pixels, and transformed or computed according to the two-dimensional DCT. This results in a DCT coefficient composed of a DC component and AC components.

The DCT coefficient is input to a quantization circuit 62, whereby the DC component and AC components are quantized independently of each other. Image data resulting from quantization is input to an entropy encoder 64, and encoded as entropy (variable length data) using a Huffman coding table 65 or the like.

Figure 4B:
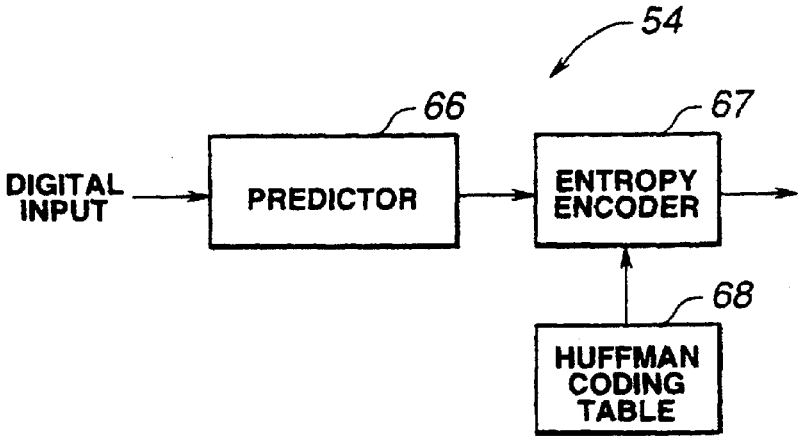

FIG. 4B shows a configuration of the JPEG compression circuit 54 of the lossless coding type. Digital image data is input to a predictor 66. The process of combining three adjoining pixels and calculating a predictive value is carried out. The predictive value is input to an entropy encoder 67. The entropy encoder 67 uses a Huffman coding table 68 to encode as entropy a value calculated by subtracting the predictive value from the value of a pixel to be encoded, or in short, a predictive error. Compared with the DCT coding, this coding suffers a low level of compressibility but enables image compression without deterioration of image quality.

Figure 5:
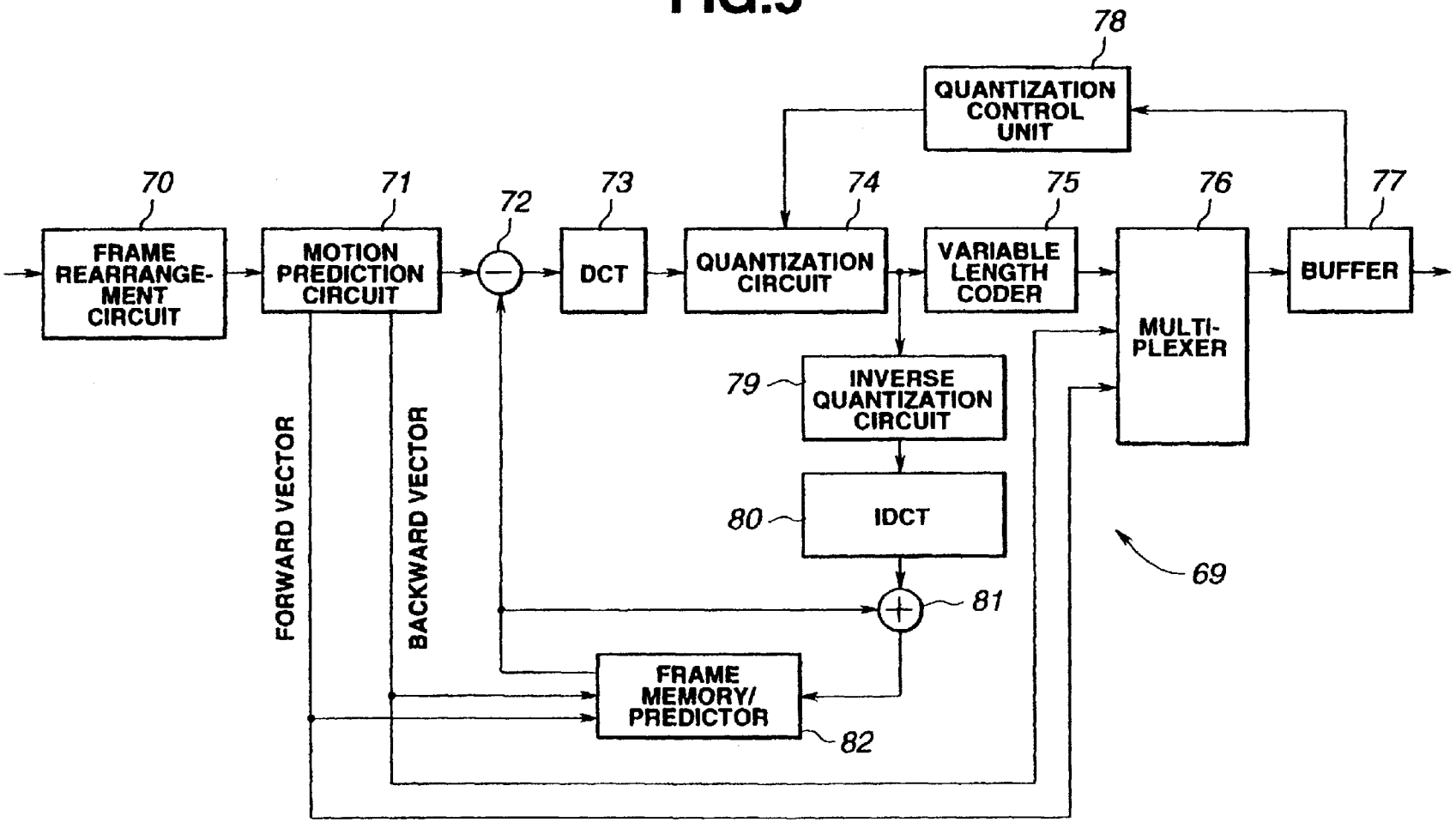

FIG. 5 shows a configuration of the motion picture-specific expansion unit 10 including an MPEG (Moving Picture Experts Group) compression circuit (or an MPEG coder) 69.

Input digital image signals R, G, and B are input to a frame rearrangement circuit 70 via a signal conversion circuit for converting each signal into a luminance signal (signal Y) and chrominance signals (signals Cr and Cb).

The MPEG compression circuit 69 divides one sequence of a motion picture into a group of pictures (GOP) consisting of a plurality of frames (pictures), and encodes the GOP. The GOP is composed of an intra-picture (I picture), predictive pictures (P pictures) that are predictive from a temporally preceding frame whose data has already been encoded, and bi-directionally predictive pictures (B pictures) that are predictive from two temporally preceding and succeeding frames.

The GOP composed of the I, P, and B pictures is subdivided into layers such as adjoining macroblocks.

Due to introduction of the plurality of picture types, the frame rearrangement circuit 70 is used to rearrange frames of an input image by picture type. Thereafter, each resultant image data is input to a motion prediction circuit 71 and subtractor 72.

Each frame data is encoded in units of a macroblock. For each macroblock, it is judged whichever of a motion compensation prediction mode or intra-picture encoding mode should be set. For the motion compensation prediction mode, the motion prediction circuit 71 compares input image data with image data provided by a frame memory/predictor 82 according to a matching method, and thus calculates forward and backward vectors. The forward and backward vectors are output to the frame memory/predictor 82. Consequently, predicted image data in which a motion has been compensated and predicted is produced and output to a multiplexer 76.

Prediction of a motion is carried out in units of a macroblock. Specifically, assuming that one block is regarded as 8 by 8 pixels, one macroblock consists of four adjoining blocks of signals Y, and one block of a signal Cr and one block of a signal Cb which are coincident with the four blocks. The subtractor 72 calculates a difference and produces a predictive error signal. The predictive error signal is input to a DCT circuit 73.

Moreover, for the intra-picture encoding mode in which compensation and prediction of a motion is not carried out, image data in which frames have been rearranged is input to the DCT circuit 73.

The DCT circuit 73 performs two-dimensional DCT in units of one block of 8 pixels by 8 lines. An output (transform coefficient) of the DCT circuit 73 is input to a quantization circuit 74. The quantization circuit 74 re-quantizes the transform coefficient with respect to a given quantization coefficient, thus minimizing the redundancy of a signal representing one block.

Quantized data output from the quantization circuit 74 is input to a variable length coder 75. The variable length coder 75 encodes the data according to the Huffman coding according to the statistics of quantized output. Specifically, a short bit is assigned to data whose frequency of occurrence is high, and a long bit is assigned to data whose frequency of occurrence is low. Thus, an amount of transmitted data is reduced.

An output of the variable length coder 75 is input to the multiplexer 76. Signals Y, Cr, and Cb are multiplexed. Coded data is then output as a bit stream through a buffer 77. The coded data is input to a quantization control unit 78. The quantization control unit 78 monitors an amount of coded data, controls a quantization coefficient set in the quantization circuit 74, and thus adjusts an amount of output data.

Moreover, quantized data output from the quantization circuit 74 is used as reference image data for motion compensation and prediction. The quantized data is therefore input to an inverse quantization circuit 79 and inversely quantized. Resultant data is input to an inverse DCT circuit 80 and subjected to inverse DCT. Thus, the processing of restoring the data to original image data is carried out.

An output of the inverse DCT circuit 80 is input to an adder 81. If necessary, the output is added to image data representing a difference and residing in the frame memory/predictor 82. Resultant data is stored in a frame memory in the frame memory/predictor 82. Reference image data in which a motion has been compensated and predicted is produced and utilized for motion compensation and prediction.

Aside from a flash memory card and a hard disk of type III, small memory cards shown in FIGS. 6A, 6B, 6C, and 6D may be used as the PC card 12 to be loaded into the PC card slot 11 of the still image-specific expansion unit 9 so that it can be unloaded freely, and to be used to store (record) a still image.

Figure 6A:
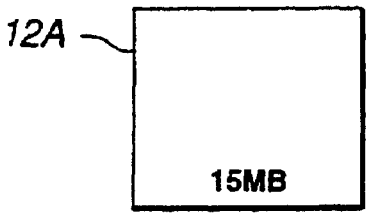
FIGS. 6A to 6D are diagrams showing small memory cards including a compact flash memory card.
Figure 6B:
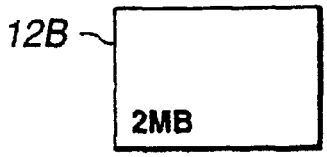
Figure 6D:
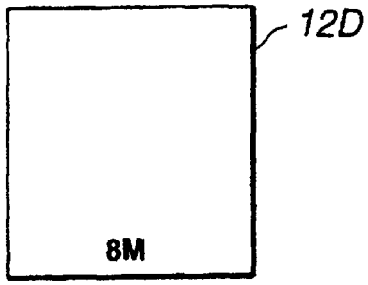
Figure 6C:
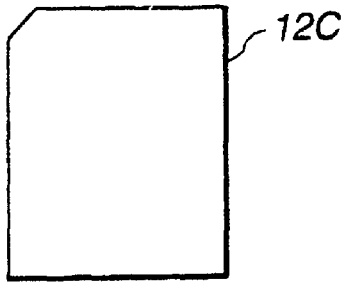

FIGS. 6A, 6B, 6C, and 6D show a compact flash memory card 12A, a miniature card 12B, a smart medium 12C, and a small PC card 12D respectively. The storage capacities shown in FIGS. 6A, 6B, and 6D are the storage capacities of locally procurable cards and are presented as practical examples of the capacities thereof.

These small memory cards have dimensions smaller than the dimensions (size) of an ordinary PC card. The small memory cards are commercialized as recording media to be used when cards smaller than the ordinary PC card are needed. When the small memory cards are used as PC cards, they are loaded into the PC card slot 11 using adapters. By attaching the adapters, the small memory cards become nearly equivalent to the PC card serving as a flash memory.

Figure 7A:
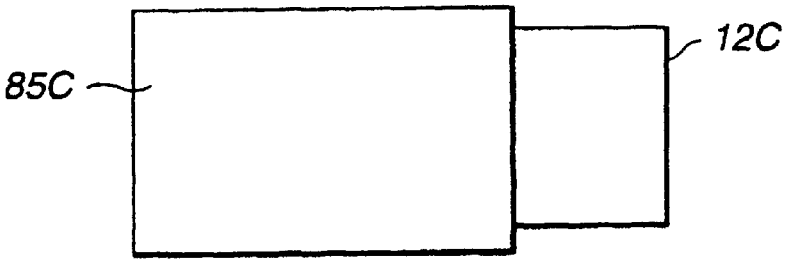
FIGS. 7A and 7B are diagrams showing adapters used to couple a small memory card to a PC card slot.
Figure 7B:
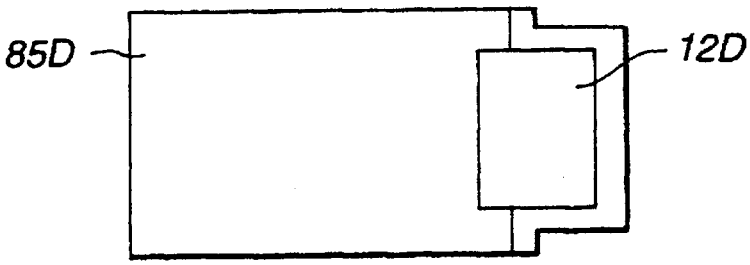

For example, as shown in FIG. 7A, the smart medium 12C is loaded via a smart medium adapter 85C. The small PC card 12D shown in FIG. 7B is loaded via a small PC card adapter 85D. The same applies to the other small cards.

In this embodiment, as mentioned above, the CCU 6 is provided with the digital video output terminal 8 to which the connector 15A or 16A of the still image-specific expansion unit 9 or motion picture-specific expansion unit 10 is coupled. When the still image-specific expansion unit 9 is connected, still image data can be recorded on the PC card 12. When the motion picture-specific expansion unit 10 is connected, motion picture data can be recorded on a DVD or the like through the digital output terminal 17 of the motion picture-specific expansion unit 10.

In FIG. 2, the CCU 6 has the frame memory 45. Alternatively, the frame memory 45 may be incorporated in the still image-specific expansion unit 9. In this case, only a digital signal representing a motion picture is output from the CCU 6 to the expansion unit.

The operations of the thus configured first embodiment will be described below.

For example, when the abdomen is operated on under endoscopic observation, the TV camera 3 is, as shown in FIG. 1, mounted on the rigid endoscope 2. The light guide cable 24 and camera cable 33 are coupled to the light source apparatus 5 and CCU 6 respectively. The color monitor 7 is connected to the CCU 6 over a monitor cable.

Moreover, the connector 15A of the cable 15 extending from, for example, the still image-specific expansion unit 9 is coupled to the digital video output terminal 8 of the CCU 6. The PC card 12 such as a hard disk of type III or the small memory card shown in FIG. 6A is coupled to the PC card slot 11 via an adapter.

The small-scale system configuration enables construction of an endoscope system having a facility for recording digital data of a still image.

The insertion unit 21 of the rigid endoscope 2 is thrust into the patient's abdomen by piercing the abdominal wall with a trocar and cannula. This makes it possible to observe a lesion in an organ or the like in the abdomen through the objective lens 27. An (endoscopic) image is then displayed on the color monitor 7. An operator views the image. When the operator judges that surgery is required, if he/she wants to record the image as a pre-operative image, he/she presses the release switch 48 or still-image release switch 48a.

A release instruction signal is input to the CPU 49. The CPU 49 inhibits writing of image data in the frame memory 45. Thus, a still image-preserved state is established. A release signal used to record a still image is sent to the still image-specific expansion unit 9 over the communication line 51.

The still-image expansion unit 9 compresses image data of a still image existent in the frame memory 45, and records resultant data on the PC card 12. The recorded information is sent to the CPU 49 over the communication line 51. The CPU 49 releases inhibition of writing of image data in the frame memory 45, and displays a message saying that one frame has been recorded on the display LED 47.

Thus, for example, a plurality of frame images can be recorded.

Moreover, a treatment instrument may be thrust into the abdomen for treatment of a lesion. During surgery or at the completion of surgery, a plurality of frame images can be recorded. Moreover, when an endoscopic examination is conducted in order to evaluate the cured state of the lesion at the completion of surgery, the images can be recorded in the same manner.

Figure 8A:
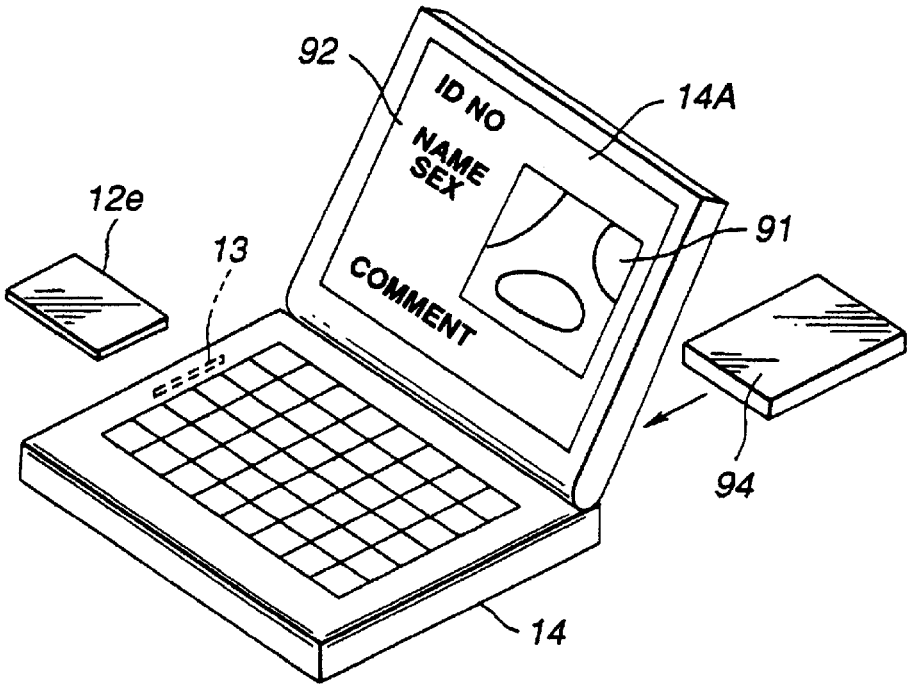

FIG. 8A shows a state in which the hard disk 12e of type III on which a still image is recorded is inserted (as the PC card 12) in the PC card slot 13 of the personal computer 14, and data of the still image is edited or manipulated.

The hard disk 12e of type III on which a still image is stored (recorded) by the still image-specific expansion unit 9 is inserted (loaded) into the PC card slot 13 of the personal computer 14. Image data compressed and stored on the hard disk 12e of type III is stretched or decoded by the personal computer 14 having the capability of a JPEG stretching circuit (or a JPEG decoder) in the form of software, and thus restored. An endoscopic image 91 represented by the resultant image data is, as shown in FIG. 8A, displayed in, for example, the right-hand area on the display surface 14A.

The ID number of a patient associated with the endoscopic image 91 is entered at the keyboard. Necessary patient data 92 is superimposed on the endoscopic image on the display surface 14A. Thus, the patient's clinical record can be created readily. The patient's clinical record can be stored on a recording means such as a hard disk incorporated in the personal computer 14 or a large-capacity hard disk 94 or magneto-optical disk (not shown) capable of being coupled to the personal computer 14 so that it can be uncoupled freely. Alternatively, a hard copy of the clinical record can be produced using a printer.

Moreover, when slides or the like must be created for use at a medical association, they can be created readily. For compiling image data as a data base, editing such as sorting of images or deletion of an image can be achieved readily. Moreover, filing can be achieved more readily than filing of photographs taken according to a prior art device or outputs of a video printer. Moreover, retrieval of any image can be achieved readily. Besides, even when re-editing or re-manipulation must be performed afterward, it can be achieved readily.

As mentioned above, recorded data of still images can be edited or manipulated readily. At this time, image quality will not be deteriorated. Moreover, when a notebook-type or portable personal computer is used as the personal computer 14, editing can be carried out at almost any place. Moreover, data of still images is compressed and stored. Image data acquired during one ordinary examination can be stored on the small PC card 12 or even a smaller small memory card.

Moreover, a general-purpose image compression circuit rather than a special image compression circuit is employed. Image compression can be achieved at low cost. Editing of image data by the personal computer 14 can be achieved readily.

Furthermore, the CCU 6 is configured in such a way that the expansion unit 9 or 10 is not incorporated in the CCU 6 but can be coupled to the digital video output terminal 8 in a freely detachable manner. The CCU 6 can be realized at cost not largely different from an existing CCU. The CCU 6 can be provided for users at a low price.

A user can select any of the expansion units 9, 10, and 97 for actual use. Moreover, when the components of the expansion unit 9, 10, or 97 are modified, the modification involves only the expansion unit 9, 10, or 97. This is advantageous. Thus, innovation can be achieved readily.

When image data recorded on the PC card 12 is stored on a recording medium such as the hard disk 94 or magneto-optical optical disk, the image data recorded on the PC card 12 is deleted. The PC card 12 can then be used to record new image data.

Figure 8B:
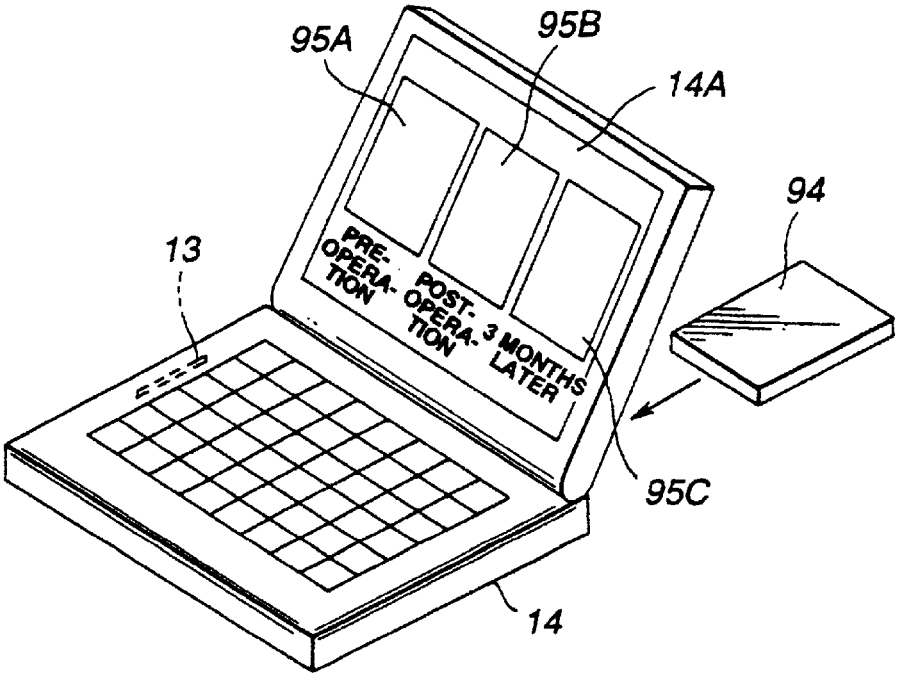

Moreover, a plurality of endoscopic images whose data has been stored on the recording medium can be displayed on the display surface 14A of the personal computer 14. For example, as shown in FIG. 8B, a pre-operative image 95A, a post-operative (immediately after surgery) image 95B, and an image 95C produced in three months after surgery may be, as shown in FIG. 8B, displayed side by side. This makes it possible to clearly observe a temporal change in a lesion cured by conducting surgery.

When a plurality of images are thus displayed side by side, the image data may be manipulated so that a portion of each image other than a portion depicting a region of interest concerned will be cut out, and images depicting the region of interest alone will be displayed. A comment or the like may be superimposed on the images.

Even when image data is thus stored (copied into) on another recording means or recording medium, image quality will not deteriorate. Moreover, when image data is manipulated, unlike when analog image data is manipulated, deterioration of image quality can be avoided nearly completely.

Furthermore, when the motion picture-specific expansion unit 10 is connected to the CCU 6 for use, motion picture data can be recorded on a DVD or the like with little deterioration of image quality. Moreover, the motion picture data recorded on the DVD may be input to the personal computer 14 and edited or manipulated. In this case, since the data is digital image data, unlike when analog image data is handled, editing will hardly deteriorate image quality.

According to this embodiment, unlike a prior art device according to which motion picture data is recorded on an analog basis, the motion picture data is recorded digitally. The motion picture data can therefore be recorded with little deterioration of image quality. Even editing will hardly deteriorate image quality.

Moreover, when the personal computer 14 or the like is employed, editing or manipulation of still image data or motion picture data can be achieved readily. Unlike when photographs are handled, recorded data of a still image can be reproduced shortly.

When the circuitry shown in FIG. 4B is adopted for the JPEG compression circuit 54, a level of compressibility is, as mentioned above, lowered. However, decompression results in perfect restoration into an image whose data has not been compressed.

According to the first embodiment, the release switch 48 is included in the CCU 6. Alternatively, the release switch 48 may be included in an endoscope or, for example, the TV camera 3. In another example, foot switch may be spliced to a cord extending from the CCU 6, whereupon a release signal may be generated by handling the foot switch to help an operator carry out releasing.

According to the first embodiment, the TV camera-mounted endoscope 4 is adopted as an endoscope including an imaging means. A simultaneous electronic endoscope in which a CCD 32 having a mosaic filter 32a or the like is located at the image formation position of the objective lens 27 in the rigid endoscope 2 shown in FIG. 2 may be substituted for the TV camera-mounted endoscope 4.

Incidentally, according to the first embodiment, the MPEG compression circuit 69 is used to compress motion picture data. The present invention is not limited to the MPEG compression circuit. For example, DV-format compression where intra-frame compression based on DCT is carried out (almost the same as the JPEG compression based on DCT. However, the length of data of each frame is not variable but fixed so that the data can be readily recorded on a tape-like recording medium) may be adopted. A DV terminal conformable to, for example, the IEEE 1394 may be used as the digital output terminal 17.

Figure 9A:
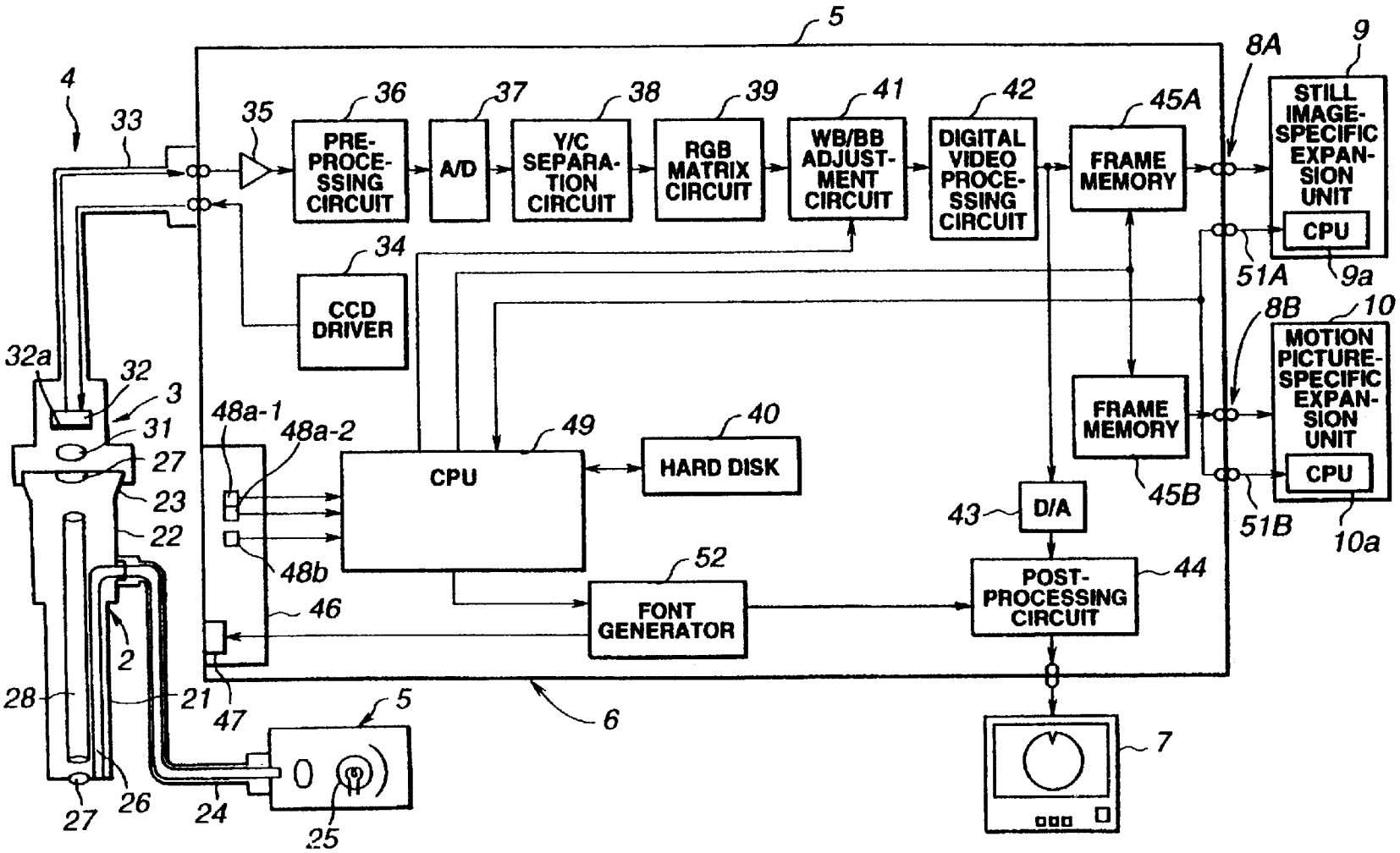
FIG. 9A is a block diagram showing a configuration of a CCU and the like in a variant of the first embodiment.

FIG. 9A shows a configuration of the CCU 6 and other apparatuses in accordance with a variant of the present invention. According to this variant, two frame memories 45A and 45B are substituted for the frame memory 45 in the CCU 6 shown in FIG. 2. Moreover, a still-image digital video output terminal 8A coupled to an output terminal of the frame memory 45A and a motion-picture digital video output terminal 8B coupled to an output terminal of the frame memory 45B are substituted for the digital video output terminal 8 coupled to the output terminal of the frame memory 45. Thus, the still image-specific expansion unit 9 and motion picture-specific expansion unit 10 can be connected simultaneously.

Moreover, the CPU 49 is designed to be able to communicate bi-directionally with CPUs 9a and 10a in the still image-specific expansion unit 9 and motion picture-specific expansion unit 10 over communication lines 51A and 51B.

According to this embodiment, the CCU 6 is provided with a hard disk 40 connected to the CPU 49. The CPU 49 receives image data, which has been compressed and stored on the PC card 12, from the CPU 9a in the still image-specific expansion unit 9 over the communication line 51A. The CPU 49 then stores the image data on the hard disk 40.

Moreover, according to this embodiment, a still image release switch 48a-1 or 48a-2 and a motion picture-specific release switch 48b are included. By handling the still image release switch 48a-1, the release signal instructing storage of image data, which has been compressed according to the lossy coding by means of the circuitry shown in FIG. 4A, on the PC card 12 is generated. By handling the still image release switch 48a-2, the release signal instructing storage of image data, which has been compressed according to the lossless coding by means of the circuitry shown in FIG. 4B, on the PC card 12 is generated.

In short, for recording a still image, an operator can select either of the circuitry shown in FIG. 4A and that shown in FIG. 4B for compression.

The other components are identical to those shown in FIG. 2. The major operation performed by this variant will be described below.

When an endoscopic examination is conducted in a connected state shown in FIG. 9A, image data of the same frame of a motion picture is usually stored in the two frame memories 45A and 45B. In this state, when an operator handles the still image release switch 48a-1, the release signal instructing storage of image data which has been compressed according to the lossy coding on the PC card 12 is output. The CPU 49 brings the frame memory 45A alone to a write-inhibited state and establishes a state in which still image data is recorded in the frame memory 45A. The CPU 49 then sends the release signal to the CPU 9a in the still image-specific expansion unit 9 over the communication line 51A.

Image data of a still image recorded in the frame memory 45A is compressed according to the lossy coding and stored on the PC card 12. When the storage operation is completed, the CPU 9a sends a completion signal to the CPU 49 over the communication line 51A. The CPU 49 releases the still image-preserved state of the frame memory 45. Specifically, write-inhibition is released, and the frame memory 45A is reset to a state in which motion picture data is recorded. Moreover, the CPU 49 displays a message saying that one frame has been recorded on the display LED 47.

Moreover, according to this embodiment, the CPU 49 instructs the CPU 9a to transfer image data, which has been compressed and recorded on the PC card 12, over the communication line 51A. The CPU 9a transfers the image data, which has been compressed and recorded on the PC card 12, to the CPU 49 over the communication line 51A at a given transfer rate according to the serial data transmission.

The CPU 49 transfers the transferred image data to the hard disk 40. Upon completion of transfer of image data of one frame, the CPU 9a sends a completion signal to terminate image data transfer.

In this embodiment, image data recorded on the PC card 12 is recorded as a backup copy on the hard disk 40 in the CCU 6. Supposing the storage capacity of the PC card 12 is exceeded by recording image data, no data would be lost.

The other operations are nearly identical to those of the first embodiment. The description of those operations will thus be omitted.

Incidentally, when still image data is recorded by releasing the still image-preserved state, the still image-specific expansion unit 9 may calculate an amount of compressed image data, of the still image and send the information to the CPU 49 over the communication line 51A. The CPU 49 may display on the display LED 47 the number of frames as well as an amount of frame data recorded (an amount of used data) or an amount of recordable capacity remaining on the PC card 12.

Information such as the number of recorded frames is displayed on the display LED 47 of the CCU 6. The information may also be displayed on the display surface of the color monitor 7 viewed by an operator. In this case, a superimposition circuit is installed in the output side of the post-processing circuit 44 to which an output of the font generator 52 is sent. Information such as the number of frames is superimposed on data represented by a video signal output from the post-processing circuit 44.

Next, a second embodiment of the present invention will be described with reference to FIG. 9B. An endoscopic imaging system 101 of this embodiment shown in FIG. 9B comprises an electronic endoscope 102 of a surface sequential imaging type, a light source unit 103 of the surface sequential type for supplying illumination light to a light guide 119 in the electronic endoscope 102, a CCU 104 of the surface sequential type for processing a signal sent from a solid-state imaging device (118) incorporated in the electronic endoscope 102, a color monitor 105, and an expansion unit 107 coupled to a digital video output terminal 106 of the CCU 104.

The electronic endoscope 102 has an elongated insertion unit 111. A large-diameter operation unit 112 is formed at the back end of the insertion unit 111. A universal cord 113 and light guide cord 114 are extending laterally from the operation unit 112. A connector 115 capable to being coupled to the CCU 104 is spliced to the proximal end of the universal cord 113.

A rigid distal part 116 and a bending portion capable of being angled and formed adjacently behind the distal part 116 together form the distal portion of the insertion unit 111. The operation unit 112 is provided with an angling knob that is not shown. By turning the angling knob, the bending portion can be angled in vertical and lateral directions.

Moreover, an objective lens 117 and SID 118 are incorporated in the distal part 116. A light guide 119 over which illumination light is propagated lies through the insertion unit 111.

The light source unit 103 to which a connector spliced to one end of the light guide cord 114 is coupled has a white light source 121 such as a xenon lamp. White light emitted from the white light source 121 is converged by a lens 122. The white light is then recomposed into sequential light rays of red, green, and blue by a rotary filter 123 that rotates at a speed agreeing with the frame frequency of a video signal (29.97 Hz in the NTSC system). The light rays are irradiated to an object 124 such as an intracorporeal organ to be observed by way of the light guide 119 and a light distribution lens 120 opposed to the distal end of the light guide 119.

Rotation of a motor 125 for rotating the rotary filter 123 is controlled by a motor servo circuit 126 so that the rotating speed will agree with the frame frequency of a video signal.

Light reflected from the object 124 passes through the objective lens 117 and forms an image on the image plane of the SID 118. With application of a clock signal for use in reading by a driver 127, the optical image is photoelectrically converted. Surface sequential signals R, G, and B are then output.

An SID driving signal sent from an SID timing signal generator 129, to which a reference clock generated by a synchronizing (hereinafter sync) signal generator 128 is input, is input to the driver 127 via an isolation photocoupler 130. A reference signal (not shown) is supplied from the sync signal generator 128 to the motor servo circuit 126. Thus, all signals (operations) are phased and synchronized with one another.

The surface sequential signals R, G, and B output from the SID 118 are amplified by a preamplifier 131 in the CCU 104. Resultant signals are input to a reset noise canceling circuit 134 via an isolation drive circuit 132 and an isolation high-frequency transformer 133 for protecting a patient from an electric shock or the like. Unnecessary components are removed from the surface sequential signals by means of a low-pass filter (LPF) 135. Resultant signals are then subjected to vertical contour correction by a vertical contour correction circuit 136 and to gamma correction by a gamma correction circuit 137.

Output signals of the gamma correction circuit 137 are converted into digital signals by an A/D converter 138. Signals read under the red, green, and blue rays of illumination light and constituting one frame are stored in a red (R) memory 139R, green (G) memory 139G, and blue (B) memory 139B which are associated with the light rays used for surface-sequential imaging.

The signals stored in the red memory 139R, green memory 139G, and blue memory 139B are read simultaneously to be timed color signals. The color signals are converted into analog signals by D/A converters 140. A conversion rate at which the A/D converter 138 converts an analog signal into a digital signal, and writing and reading of data into or from the red memory 139R, green memory 139G, and blue memory 139B are controlled with an output signal of a memory control circuit 141.

The analog color signals R, G, and B output from the D/A converters 140 have unnecessary components thereof removed by LPFs 142. Resultant signals are input to horizontal contour correction circuits 143. After subjected to horizontal contour correction, the signals are amplified by output amplifiers 144. Resultant signals are output as three elementary color signals R, G, and B, of which output impedance is, for example, 75Ω, to a monitor 105 or the like through the red, green, and blue output terminals. Moreover, a sync signal generated by the sync signal generator 128 is also amplified by an output amplifier 145, and output as a sync signal SYNC, of which output impedance is, for example, 75Ω, to the monitor 105 or the like through a sync output terminal.

Moreover, the signals R, G, and B that have been timed and subjected to horizontal contour correction are used to produce a luminance signal Y by means of a Y matrix circuit 146. The luminance signal Y and color signal R are used to produce a chrominance signal R-Y by means of an R-Y matrix circuit 147. The luminance signal Y and color signal B are used to produce a chrominance signal B-Y by means of a B-Y matrix circuit 148.

The chrominance signals R-Y and B-Y are subjected to balanced modulation, where subcarriers (having a frequency of 3.1129545 MHz and being 90° out of phase) are employed, by means of encoders 149 and 150. Resultant signals are synthesized into vector by an adder 151. This results in a chrominance signal C. The chrominance signal C is multiplexed with the luminance signal Y by a synthetic output amplifier 152. Furthermore, a composite sync signal and color burst are appended to the multiplexed signal. Consequently, a composite video signal that is an NTSC signal is produced and output to the monitor through an NTSC output pin of a connector 153.

By the way, a patient circuit unit 154 composed of the driver 127, preamplifier 131, and isolation drive circuit 132 in the CCU 104 is shielded by a shield case 155. A signal input/output unit 156 on the succeeding side of the patient circuit unit, which is isolated by the photocoupler 130 and high-frequency transformer 133 which serve as an isolation means, is also shielded with a shield case 157 separately from the shield case 155.

Moreover, outputs of the red memory 139R, green memory 139G, and blue memory 139B are output to an expansion unit 107 through a digital video output terminal 106. A CPU, which is not shown, in the expansion unit 107 is connected to the CPU 155 in the CCU 104 over a bi-directional communication line 156.

Either a still image-specific expansion unit or a motion picture-specific expansion unit can be connected as the expansion unit 107 as described in the first embodiment.

Moreover, for example, a front panel 157 of the CCU 104 is provided with a release switch 158. When the release switch 158 is turned on, the CPU 155 sends a release signal to the expansion unit 107 over the communication line 156. The expansion unit 107 carries out an image recording operation.

In this case, when the expansion unit 107 is a still image-specific expansion unit, still image data of one frame is stored on a PC card loaded into the still image-specific expansion unit. By contrast, when the expansion unit 107 is a motion picture-specific expansion unit, motion picture data is compressed and output to peripheral equipment such as a DVD coupled to the digital output terminal of the motion picture-specific expansion unit through the digital output terminal. A release signal is also output to the peripheral equipment.

Figure 9B:
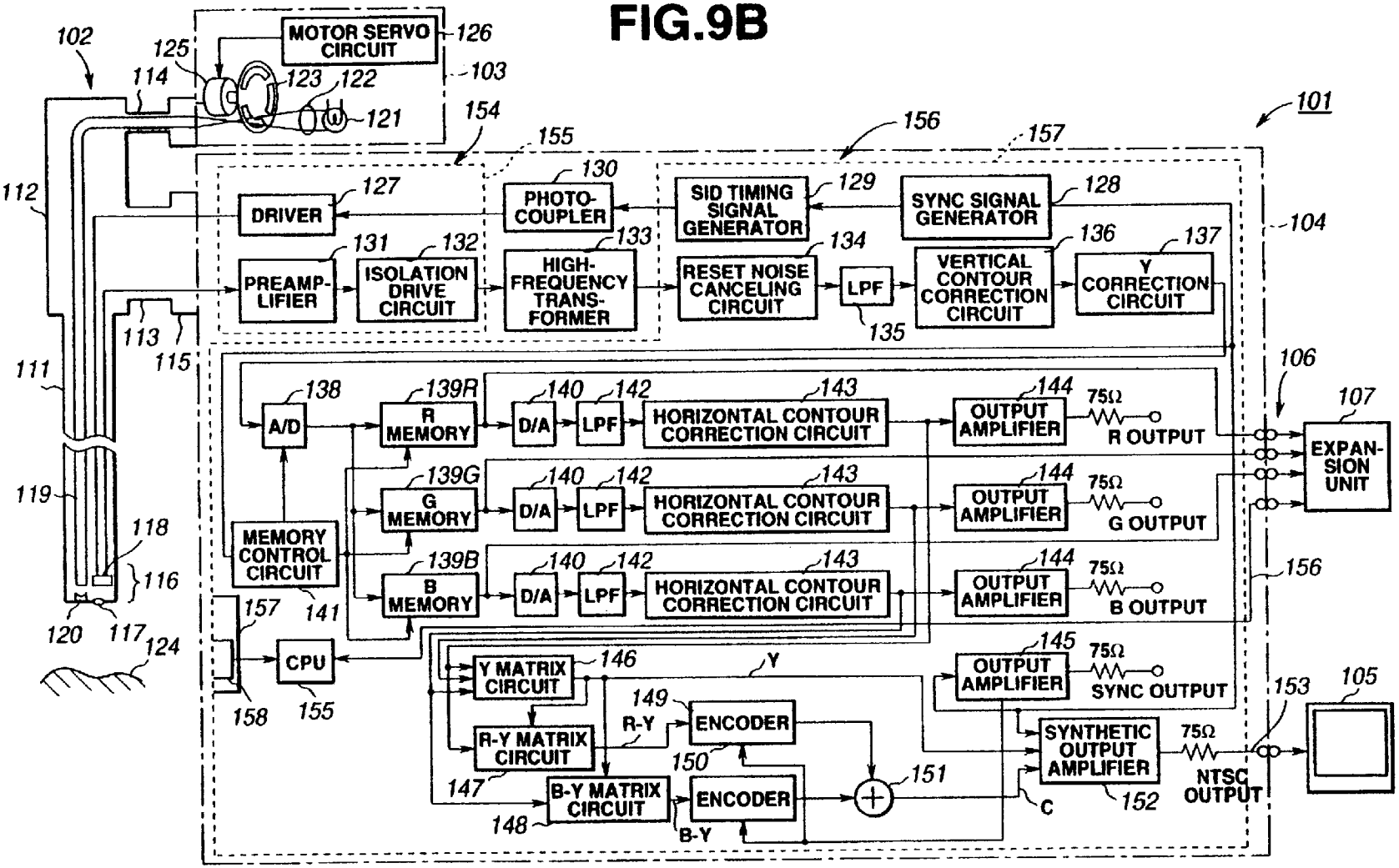
FIG. 9B is a block diagram showing a configuration of an endoscopic imaging system of a second embodiment of the present invention.

Incidentally, the CCU 104 shown in FIG. 9B may be provided with the display LED 47 shown in FIG. 2.

The first embodiment adopts the simultaneous imaging type imaging system (comprising, particularly, the light source apparatus 5 for outputting white light, the simultaneous imaging type TV camera-mounted endoscope 4, and the CCU 6 serving as a simultaneous imaging type signal processing means). By contrast, this embodiment adopts the surface sequential imaging type imaging system (comprising the light source unit 103 for outputting surface-sequential light, the surface sequential imaging type electronic endoscope 102, and the CCU 104 serving as a signal processing means for processing a signal sent from the surface sequential imaging type imaging means).

Consequently, the operations and advantages other than those of a portion for illuminating and visualizing an object surface-sequentially and a portion for processing a signal are identical those of the first embodiment.

Next, a third embodiment of the present invention will be described with reference to FIGS. 10 and 11.

Figure 10:
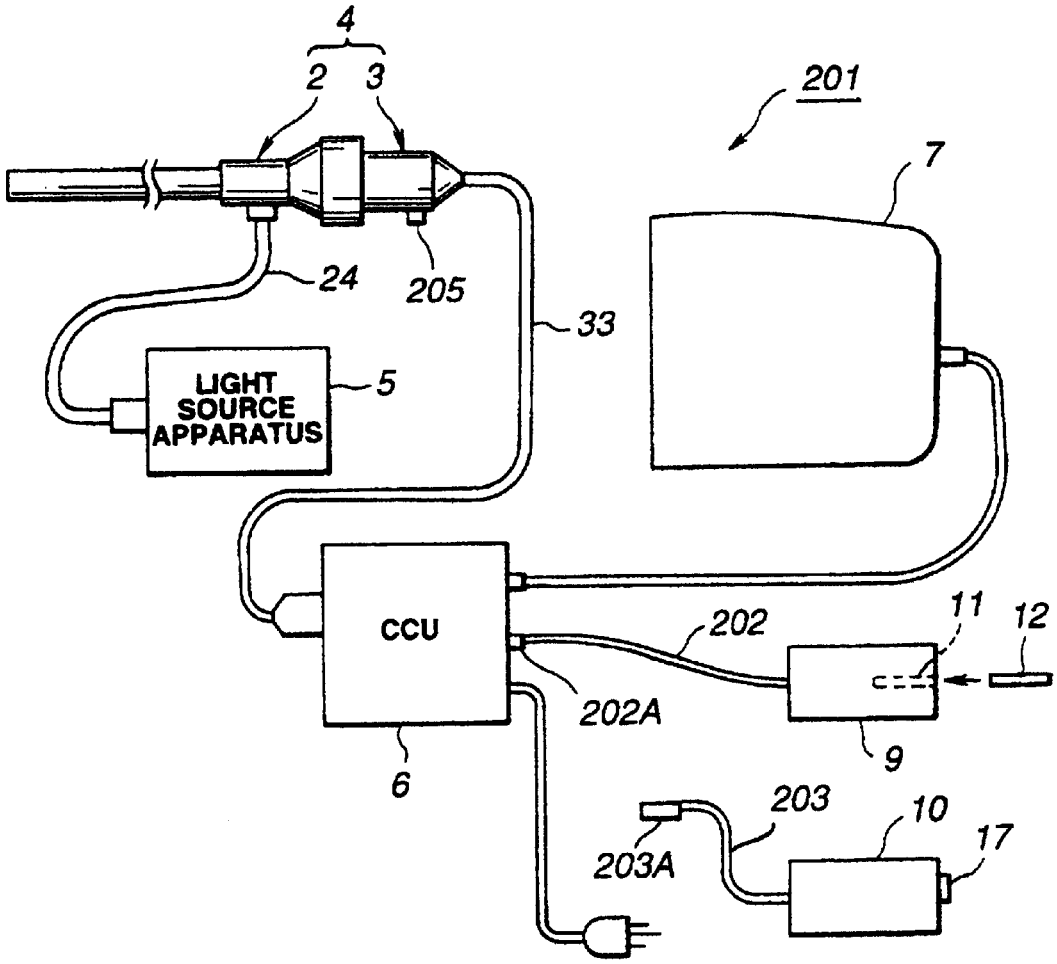
FIG. 10 is an oblique view showing a configuration of an endoscopic imaging system of a third embodiment of the present invention.

An endoscopic imaging system 201 of the third embodiment shown in FIG. 10 has the same fundamental configuration as the first embodiment shown in FIG. 1. The endoscopic imaging system 201 comprises a TV camera-mounted endoscope 4 having a TV camera 3 mounted on a rigid endoscope 2, a light source apparatus 5 for supplying illumination light to the rigid endoscope 2, a CCU 6 for processing a signal sent from an imaging means in the TV camera 3, a color monitor 7 for displaying an image represented by a video signal output from the CCU 6, a still image-specific expansion unit 9 and motion picture-specific expansion unit 10 which are attachable to a digital video output terminal 8 (not shown in FIG. 10) of the CCU 6 so that they can be uncoupled freely, and a personal computer, which is not shown, having a PC card slot into which a PC card 12 is designed to be loaded into a PC card slot 11 of the still image-specific expansion unit 9 so that it can be unloaded freely.

In this embodiment, the TV camera 3 is provided with a release switch 205. When the release switch 205 is turned on, a release instruction signal is input to the CPU 49 (See FIG. 2) in the CCU 6 over a camera cable 33. According to this embodiment, in addition to a release switch 48 of the CCU 6, the release switch 205 is included in the endoscope 4.

Moreover, in this embodiment, a connector 202A spliced to an end of a still image-specific expansion unit cable 202, which has the other end thereof spliced to the still image-specific expansion unit 9, is coupled to the digital video output terminal 8 of the CCU 6 in a manner in which the connector 202A can be freely uncoupled therefrom.

Moreover, a connector 203A spliced to an end of a motion picture-specific expansion unit cable 203, which has the other end thereof spliced to the motion picture-specific expansion unit 10, can be coupled to the digital video output terminal 8 of the CCU 6 in a manner in which the connector 203A can be freely uncoupled therefrom.

Moreover, in this embodiment, the CCU 6 can transfer digital data to or from the expansion unit 9 or 10 by parallel data transmission. The connector 202A serving as an interface for interfacing the CCU 6 with the still image-specific expansion unit 9 over the still image-specific expansion unit cable 202 has a structure shown in FIG. 11.

The cable 202 is, for example, a flat cable. The card edge type connector 202A is spliced to the end of the cable 202. Signal pins 211, 212, and 213 formed by plating an insulating substrate 210 with copper in the form of bands are exposed from the distal end of the connector 202A having the proximal end thereof spliced to the flat cable. In this embodiment, these signal pins 211, 212, and 213 are jutting out by different lengths according to the type of a signal applied to associated signal pins (specifically, data, power, or ground-level voltage).

Figure 11:
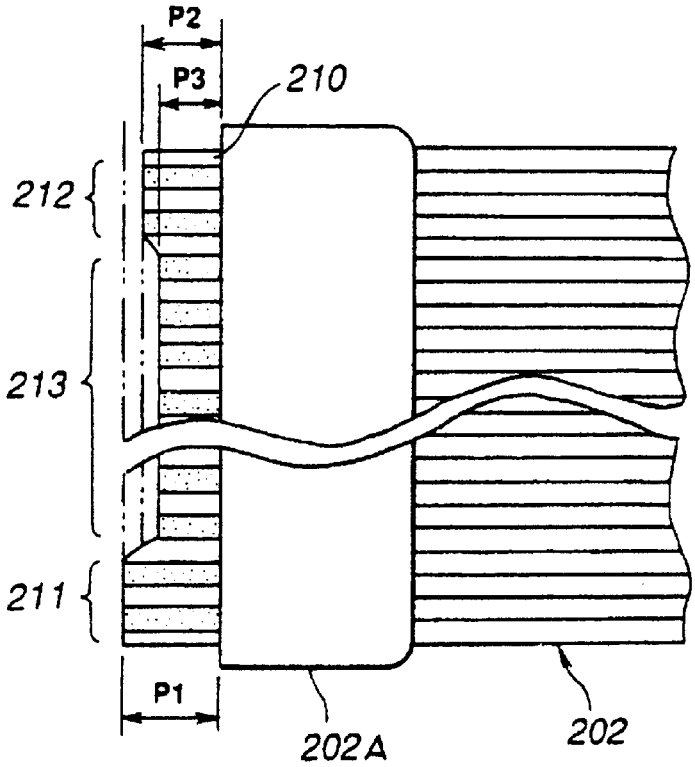
FIG. 11 is a plan view showing a structure of a connector spliced to an end of a cable.

In FIG. 11, all the signal pins 211, 212, and 213 are exposed. This is intended to clearly show the connector 202A. In reality, the signal pins are covered to prevent being touched directly with a finger or the like.

As shown in FIG. 11, the lengths of the signal pins 211, 212, and 213 formed on the upper side or lower side of the insulating substrate 210 are determined so that the length P1 of the ground pins 211 will be longer than the length P2 of the power pins 212, and the length P2 will be longer than the length P3 of the data pins 213. Two pieces of equipment (specifically, the CCU 6 and static image-specific expansion unit 9) are linked through the ground pins 211, power pins 212, and data pins 213 in that order. This results in improved safety.

In FIG. 11, when the CCU 6 and expansion unit 9 are linked, power is supplied from the CCU 6 to the expansion unit 9 via the power pins 212.

For the structure of the connector, a power cable extending from the CCU 6 is shown in FIG. 10. The plug at an end of the power cable is fitted into an electrical outlet such as a wall socket. Thus, electrical power is supplied to the CCU 6. The CCU 6 allows an internal power circuit that is not shown to generate direct current (DC) necessary for operating circuits.

By contrast, an electrical connection cable may be extended from the expansion unit 9. The expansion unit 9 may be provided with a facility for allowing an internal power circuit to supply electrical power to the internal circuits thereof. In this case, the power pins 212 shown in FIG. 11 may be excluded.

In this case, linkage is established through the ground pins 211 and then through the data pins 213. The connector 203 of the motion picture-specific expansion unit 10 has the same structure of signal pins. Specifically, the length of the ground pins is longer than that of the power pins, and the length of the power pins is larger than that of the data pins. Similarly, the power pins may be omitted when the expansion unit 10 is provided with an internal power supply facility.

Moreover, this embodiment has been described with reference to the card edge type connector 202A as an example. All parallel data transfer modes conceivable with the employment of the connector may be used in accordance with the present invention.

According to this embodiment, for transmitting digital data in the parallel transmission mode, owing to the aforesaid structure, linkage can be established through the ground pins 211, power pins 212, and data pins 213 in that order, or through the ground pins 211 and data pins 213 in that order. The safety of peripheral equipment of an endoscope to be linked mutually will improve. Eventually, the probability of failure or breakage of equipment can be minimized.

In FIG. 10, one end of each of the still image-specific expansion unit cable 202 and motion picture-specific expansion unit cable 203 are spliced to the still image-specific expansion unit 9 and motion picture-specific expansion unit 10, respectively, without intervention of a connector. The present invention is not limited to this form. A form in which the still image-specific expansion unit cable and motion picture-specific expansion unit cable are spliced to the still image-specific expansion unit 9 and motion picture-specific expansion unit 10 with connectors between them is also consistent with the concept of the present invention. In this case, when the connectors are structured as shown in FIG. 11, the aforesaid operations and advantages can be exerted.

Next, a fourth embodiment of the present invention will be described with reference to FIG. 12. In the third embodiment, the cables 202 and 203 are designed to transfer digital data in the parallel transfer mode. In this embodiment, the CCU 6 is provided with a digital data output terminal through which digital data is transferred in the serial transfer mode. Digital data is transferred to or from an expansion unit over a cable 221 having a connector 221A thereof coupled to the digital data output terminal.

Figure 12:
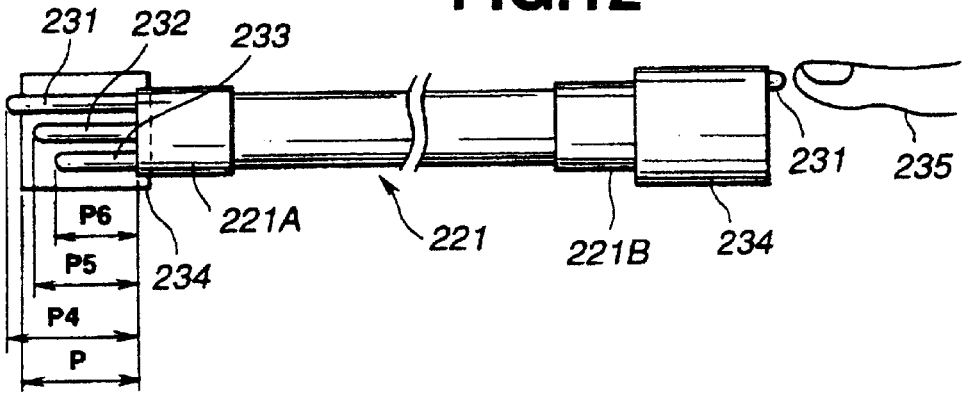
FIG. 12 is a side view showing a structure of a connector spliced to an end of a cable in a fourth embodiment of the present invention.

As shown in FIG. 12, the connector 221A at one end of the cable 221 is coupled to the digital data output terminal of the CCU 6 in a manner in which it can be uncoupled freely therefrom. A connector 221B at the other end of the cable 221 is coupled to an expansion unit. Alternatively, the cable 221 may extend directly from the expansion unit rather than being spliced to the other end of the cable.

In this embodiment, like the third embodiment, the lengths of the signal pins are differentiated depending on the type of a signal to be transmitted through a signal pin.

Specifically, the lengths of a ground pin 231, power pin 232, and data pin 233 are determined so that the length P4 of the ground pin 231 will be longer than the length P5 of the power pin 232, and the length P5 will be longer than the length P6 of the data pin 233. Consequently, linkage between the CCU 6 and the expansion unit is established through the ground pin 231, power pin 232, and data pin 233 in that order.

When the cable 221 has the foregoing structure, a connector cover 234 is, as shown in FIG. 12, used to protect the signal pins. In this case, the length P of the connector cover 234 is designed to be a little smaller than the length P4 of the ground pin 231. Owing to this design, for example, even if the cable 221 is handled with an electrically charged finger 235, the finger will touch the ground pin 231. Therefore, even if the end of the cable 221 is coupled to equipment, static electricity existent at the finger flows out to the ground. Thus, the equipment can be used more safely.

Moreover, in FIG. 12, the expansion unit is designed to receive power supplied from the CCU 6. A power cable is therefore incorporated as a conductor in the cable 221 linking the CCU 6 and expansion unit. If the expansion unit itself has a facility for receiving power externally, the power cable may be excluded from the dedicated cable.

For transmitting digital data in the serial transmission mode, owing to the aforesaid structure, linkage of equipment can be established through the ground pin 231, power pin 232, and data pin 233 in that order. The safety of equipment therefore improves. Eventually, the probability of failure and breakage of equipment can be minimized.

The form shown in FIG. 12 may be adapted to a structure including a control signal line over which a control signal is transmitted by parallel transmission in addition to the data lines. In this case, a control signal may be sent bi-directionally. For this purpose, two control signal lines may be included.

Next, a fifth embodiment of the present invention will be described with reference to FIG. 13. A fundamental configuration of this embodiment is identical to the one of the third embodiment shown in FIG. 10. Like the third embodiment, in this embodiment, the parallel transfer mode is adopted.

Figure 13A:
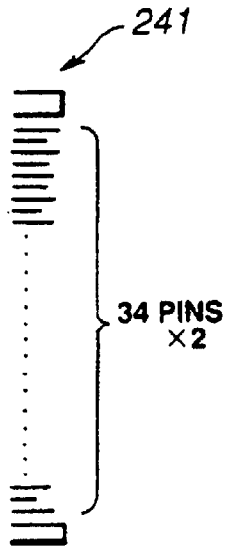
FIGS. 13A and 13B are plan views showing in enlargement the shapes of a card bus and its pins in a PC card slot in accordance with a fifth embodiment of the present invention.
Figure 13B:
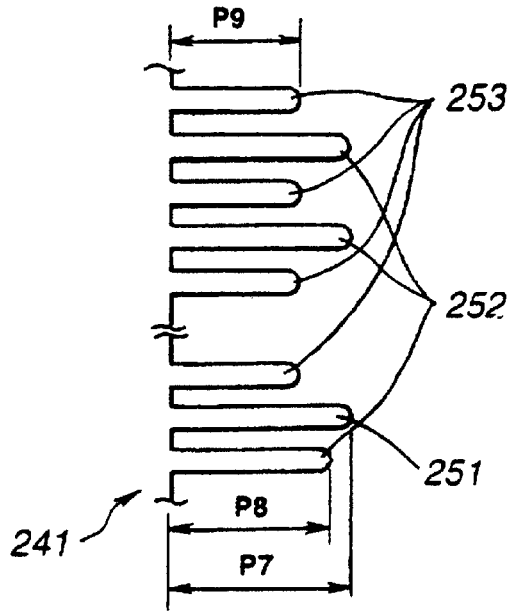

FIGS. 13A and 13B show a card bus 241 serving as a card edge type interface terminal (connector) as a simple example of this aspect of the present invention.

Unlike the aforesaid third and fourth embodiments, in this embodiment, the edge of the PC card 12 is coupled to the card bus 241 in the PC card slot 11 of the still image-specific expansion unit 9 shown in FIG. 10 so that the edge can be uncoupled freely.

The card bus 241 has two rows of 34 finely projected pins. The lengths of the pins of the card bus 241 are determined depending on a signal associated with each pin in such a manner that the length P7 of a ground pin 251 is longer than the length P8 of power pins 252 and the length P8 is longer than the length P9 of data pins 253. The lengths of the signal pins are thus different from one another. When the PC card 12 is inserted into the expansion unit 9, linkage is established through the ground pin 251, power pins 252, and data pins 253 in that order. Consequently, electrical breakdown occurring by coupling the PC card 12 can be prevented. This leads to improved reliability.

When digital data is recorded on the PC card 12 or the like, the foregoing structure helps reduce failure and breakage of equipment and improve reliability.

FIG. 5 shows briefly the configuration of an MPEG1 (ISO 11172 Video)-conformable compression circuit 69. A motion picture-specific expansion unit including an MPEG2-conformable compression circuit may be connected to record a motion picture.

For example, in the first embodiment, the still image-specific expansion unit 9 has one PC card slot 11. Alternatively, the still image-specific expansion unit 9 may be provided with two or more PC card slots 11.

Moreover, the still image-specific expansion unit 9 may be designed so that not only the PC card 12 can be coupled to (mounted in) the PC card slot 11 but also a recording medium (or memory) on which still image data is recorded can be coupled in a freely detachable manner or incorporated in the expansion unit 9.

Assume that the still image-specific expansion unit 9 is designed as mentioned above. In this case, when the storage capacity of the PC card 12 coupled to the PC card slot 11 is exceeded by recording still image data, excessive data may be recorded on the recording medium (or memory). Alternatively, when the storage capacity of the PC card 12 coupled to the PC card slot 11 is exceeded by recording still image data, a message saying that the PC card should be replaced with a new one may be displayed on the display LED 47 or on the color monitor 7. Moreover, when an amount of recorded data approaches the storage capacity of the PC card 12, a message saying that the PC card should be replaced with a new one because an amount of recorded data is close to the storage capacity of the PC card 12 may be displayed.

Moreover, the CCU 6 may be provided with a digital video output terminal through which a still-image digital video signal is output, and a digital video input terminal through which a still-image digital video signal whose data has been compressed and output from the still image-specific expansion unit 9 input. In this case, a recording medium on which the compressed still image data is recorded may be able to be coupled to the CCU 6 in a freely detachable manner, or may be incorporated therein.

Additionally, an amount of still image data exceeding the storage capacity of the PC card 12 loaded into the PC card slot may be able to be recorded by compressing the data.

Moreover, the CCU 6 may be provided with a modem or a communication means for handling serial data, which is connectable to the personal computer 14 or the like. Thus, image data recorded on a PC card coupled to the PC card slot of the CCU 6 may be able to be transferred to a large-capacity hard disk in the personal computer 14. Otherwise, image data recorded on the PC card 12 loaded into the PC card slot 11 of the expansion unit may be able to be transferred to the large-capacity hard disk in the personal computer 14.

For example, the endoscopic imaging system may be configured so that image data recorded on the PC card 12 loaded into the PC card slot 11 can be transferred to another recording means via a communication means even during an endoscopic examination. In this case, the transferred image data can be deleted from the PC card 12, and the PC card 12 can be used to record new image data The PC card 12 can therefore be used to record a large amount of image data irrespective of the storage capacity of the PC card 12.

In this case, when the communication means is used to transfer data, image data of one frame is temporarily buffered. Thereafter, the image data is transferred by the communication means designed for serial transmission. When it is instructed to record still image data even during data transfer, the still image data can be recorded immediately.

The present invention is not limited to the structure of the CCU 6 having the digital video input and output terminals through which the CCU and still image-specific expansion unit 9 are linked. Alternatively, the CCU 6 may be provided with a digital video output terminal through which a motion-picture digital video signal is output, and a digital video input terminal through which a motion-picture digital video signal whose data has been compressed and output from the motion picture-specific expansion unit 10 is input. The CCU 6 may then be structured so that a motion picture recording device such as a DVD can be coupled to the CCU 6 in a freely detachable manner.

As mentioned above, according to the first through fifth embodiments, endoscopic image data can be compressed and stored or recorded. Retrieval, editing, and manipulation of image data can therefore be achieved readily. Repeated manipulation will little deteriorate image quality. Moreover, an endoscopic imaging system can be realized on a small scale at low cost.

Next, a sixth embodiment of the present invention will be described. The sixth embodiment and thereafter provide endoscopic imaging systems having configurations in which endoscopic image data can be stored or recorded on an external storage device which has a simple structure.

Figure 14:
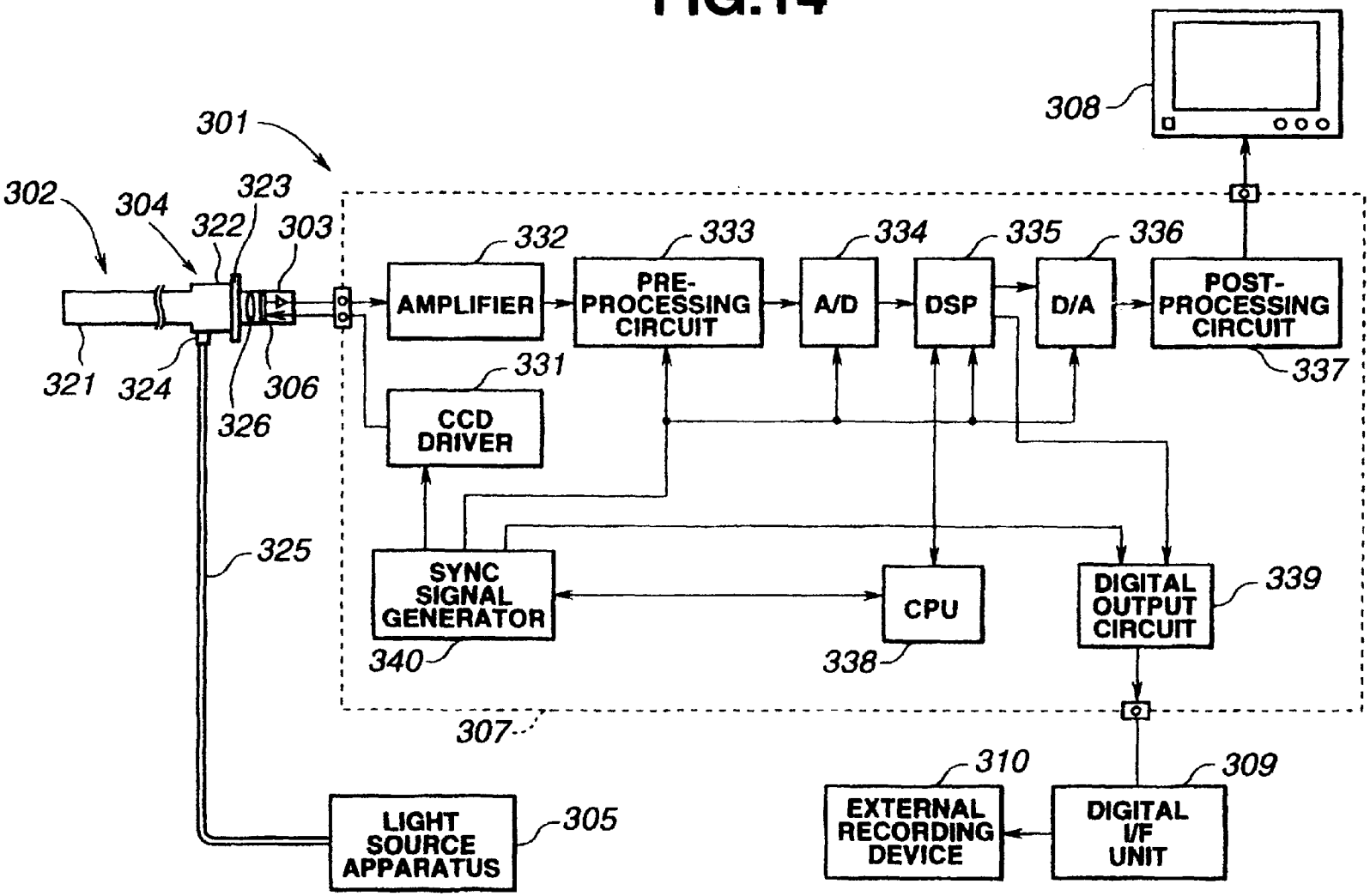
FIGS. 14 to 17 relate to a sixth embodiment of the present invention.

As shown in FIG. 14, an endoscopic imaging system 301 of this embodiment comprises a TV camera-mounted endoscope 304 having a TV camera 303 mounted on a rigid endoscope 302, a light source apparatus 305 for supplying illumination light to the rigid endoscope 302, a camera control unit (CCU) 307 for processing a signal sent from a charge-coupled device (CCD) 306 that is a solid-state imaging device incorporated in the TV camera 303, a color monitor 308 for displaying an endoscopic image represented by a video signal output from the CCU 307, and a digital interface unit 309 to be coupled to the CCU 307 so that it can also be detachable therefrom. An external storage 310, for example, a PC card is coupled to the digital interface unit 309 so that it can be detached freely.

The rigid endoscope 302 includes an elongated insertion unit 321, a hand-held unit 322 formed at the back end of the insertion unit 321, and an eyepiece unit 323 formed at the back end of the hand-held unit 322. The hand-held unit 322 is provided with a light guide base 324, and connected to the light source apparatus 305 over a light guide cable 325.

Illumination light emanating from a lamp in the light source apparatus 305 is converged by a condenser and supplied to an incident end surface of a light guide lying through the light guide cable 325, though it is not illustrated. The illumination light propagates through the light guide in the rigid endoscope 302. The illumination light is then emitted forward through the distal end of the light guide which is fitted in an illumination window in the distal part of the insertion unit 321. An object such as a lesion is thus illuminated.

Moreover, an objective lens is fitted in an observation window adjacent to the illumination window in the distal part of the insertion unit 321. The objective lens forms an object image at the image formation position thereof. The formed image is transmitted by a system of relay lenses arranged in the insertion unit 321 and opposed to the objective lens. An image is re-formed near the eyepiece unit 323. The image is then re-formed on the CCD 306 by means of an eyepiece included in the eyepiece unit 323 and an image formation lens 326 in the TV camera 303 opposed to the eyepiece.

A mosaic filter that is not shown is located in front of the image plane (photoelectric conversion plane) of the CCD 306. Color components of light incident on each pixel are optically separated from one another by the mosaic filter. In other words, the imaging means of this embodiment is a simultaneous imaging means for producing a color image signal under illumination of white light.

The CCD 306 in the TV camera 303 is connected to the CCU 307. When a CCD driving signal is applied from a CCD driver 331 in the CCU 307 to the CCD 306, a CCD output signal (image signal) photoelectrically converted and output by the CCD 306 is input to an amplifier 332 in the CCU 7. The signal amplified by the preamplifier 332 is input to a pre-processing circuit 333.

The CCD output signal input to the pre-processing circuit 333 is pre-processed by performing correlation double sampling (CDS) and sample-and-hold (S/H), and then input to an A/D converter 334. After being converted into a digital signal, the CCD output signal is input to a digital signal processor (DSP) 335.

The DSP 335 recomposes the input digital signal into digital signals Y, Cr, and Cb of three channels according to a line-sequential imaging. The digital signals are separated from one another, and converted into a digital signal RGB according to the matrix algebra. The digital signal RGB converted according to the matrix algebra is adjusted in white balance and black balance, and then processed digitally by performing enhancement, gamma correction, and character convolution. A resultant signal is input to a D/A converter 336.

The digital signal input to the D/A converter 336 is converted into an analog signal, and then converted into a standard video signal by a post-processing circuit 337. A resultant signal is output to a color monitor 308.

Moreover, a digital video signal output from the DSP 335 is also output to a digital output circuit 339 under the control of the CPU 338. The digital video signal is output to the digital interface unit 309 via the digital output circuit 339.

Moreover, the CCU 307 is provided with a sync signal generator 340 that is controlled by the CPU 338. The CCD driver 331 drives the CCD 306 synchronously with a sync signal generated by the sync signal generator 340. The sync signal generated by the sync signal generator 340 is output to each of the pre-processing circuit 333, A/D converter 334, DSP 335, D/A converter 336, and digital output circuit 339. The CCD output signal (image signal) output from the CCD driver 331 is processed synchronously with the sync signal.

Figure 15:
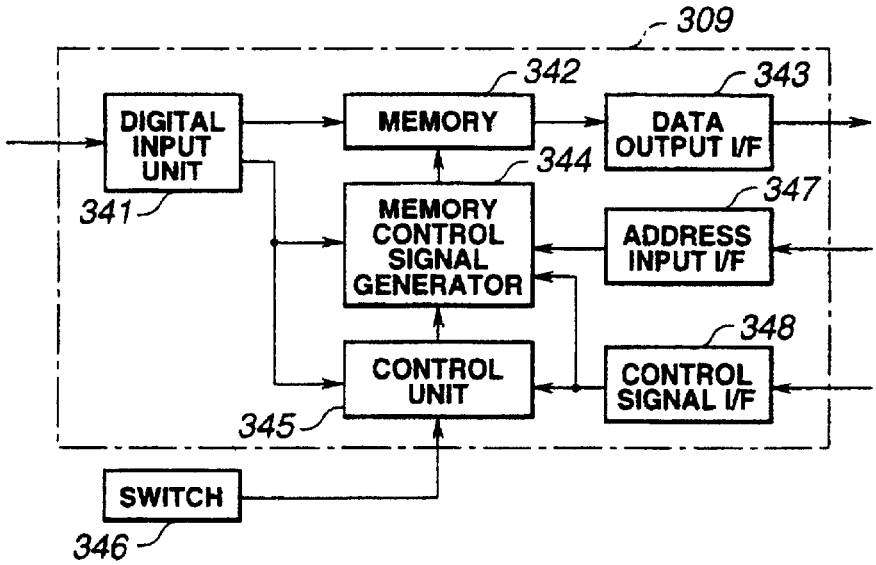

As shown in FIG. 15, the digital interface unit 309 inputs a digital video signal from digital output circuit 339 input from the DSP 335 via a digital input unit 341, and stores it in a memory 342. A digital video signal stored in the memory 342 is output to an external recording device 310 loaded into the digital interface unit 309 via a data output interface 343.

The read or write operation to be performed on a digital video signal in the memory 342 is controlled with a memory control signal generated by a memory control signal generator 344. Generation of the memory control signal by the memory control signal generator 344 is controlled by a control unit 345.

Figure 16:
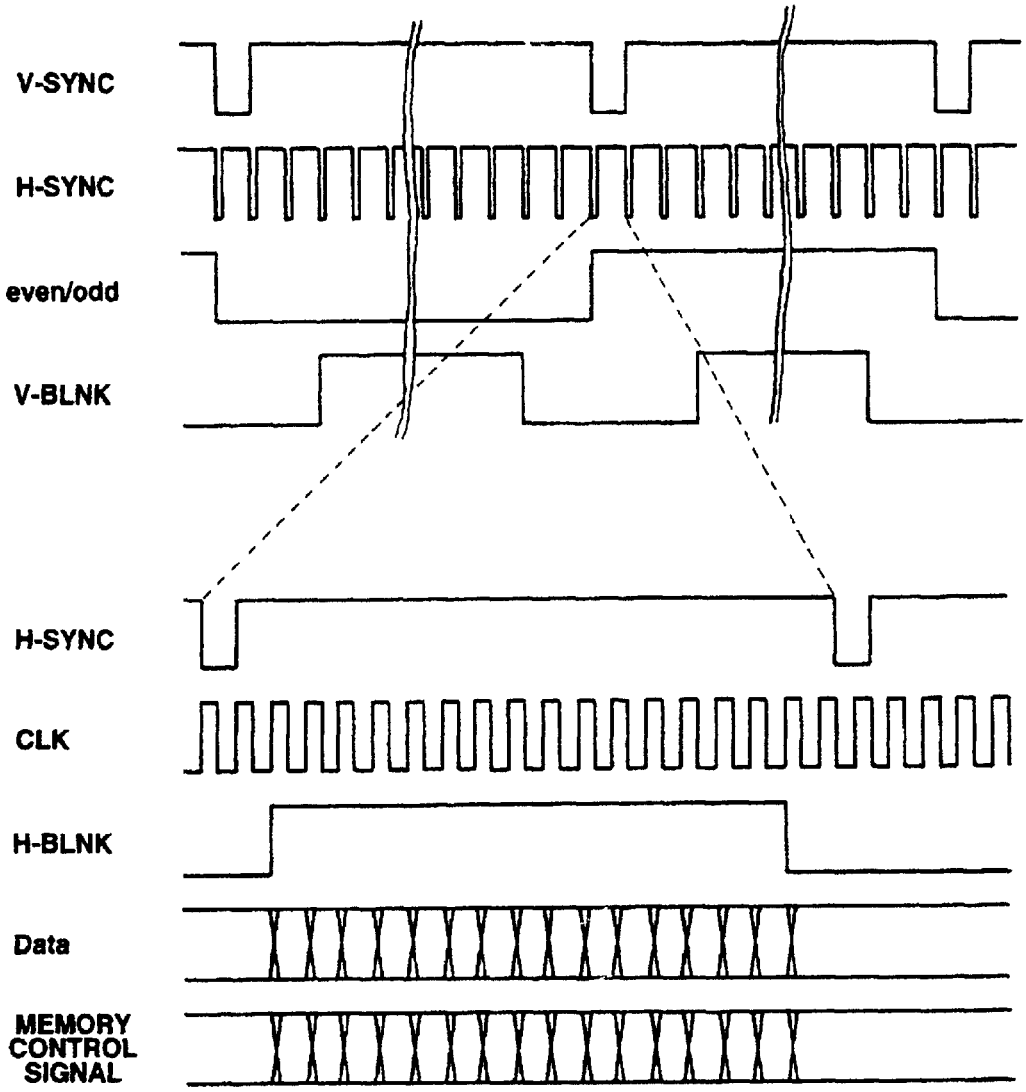

During a write operation, a vertical sync signal (V-SYNC), a horizontal sync signal (H-SYNC), a field signal (even/odd), a vertical blanking signal (V-BLNK), and a clock signal (CLK) and horizontal blanking signal (H-BLNK) which are illustrated in FIG. 16 in enlargement relative to one pulse of the horizontal sync signal, are input to the memory control signal generator 344. These signals are, as shown in FIG. 16, input together with a digital video signal (Data) sent from the DSP 335 via digital output circuit 339. The clock signal (CLK) is also input to the control unit 345.

The control unit 345 controls the memory control signal generator 344 synchronously with the clock signal (CLK) in response to an ON signal sent from a switch 346 included in the digital interface unit 309. This causes the memory control signal generator 344 to output a memory control signal that is a write signal to the memory 342. Consequently, the digital video signal is stored in the memory 342.

During a read operation, an address signal and control signal sent from the external recording device 310 are input to an address input interface 347 and a control signal interface 348. The address signal and control signal sent from the address input interface 347 and control signal interface 348 are input to the memory control signal generator 344. The control signal sent from the control signal interface 348 is also input to the control unit 345.

The control unit 345 controls the memory control signal generator 344 according to the control signal. This causes the memory control signal generator 344 to output a memory control signal that is a read signal to the memory 342. Consequently, a digital video signal is read from the memory 342, and output to the external recording device 310 via the data output interface 343.

Incidentally, a signal sent from the switch 346 is input to the control unit 345. With the input, generation of a write signal is controlled. Alternatively, generation of a write signal may be controlled responsively to a control signal sent from the CPU 338 in the CCU 307.

Figure 17:
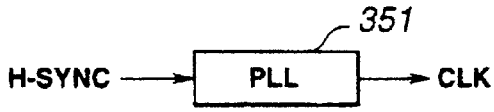

Moreover, the clock signal (CLK) is input into the digital interface unit 309 together with the digital video signal (Data) sent from the DSP 335 via the digital output circuit 339. Alternatively, as shown in FIG. 17, a PLL 351 may extract the clock signal (CLK) from the horizontal sync signal (H-SYNC). Next, the operations of the endoscopic imaging system 301 of this embodiment having the foregoing components will be described.

For example, when the abdomen is operated on under endoscopic observation, the TV camera 303 is mounted on the rigid endoscope 302, and connected to the light source apparatus 305 and CCU 307. The color monitor 308 is connected to the CCU 307. Moreover, the digital interface unit 309 is connected to the CCU 307, and the external recording device 310 is connected to the digital interface unit 309.

The insertion unit 321 of the rigid endoscope 302 is thrust into the patient's abdomen by piercing the abdominal wall with a trocar and cannula, so that a lesion in or on, for example, an organ in the abdomen can be observed. An (endoscopic) image is then displayed on the color monitor 308. An operator views the image. When an image the operator wants to record is displayed on the color monitor 308, the operator handles the switch 346 to record the image data in the memory 342 in the digital interface unit 309. By handling a hand release switch or foot switch that is not shown, the operator can record endoscopic image data on the external recording device 310 such as a PC card. Moreover, the operator can utilize the recorded image data at a personal computer in the future.

Incidentally, handling of the switch 346 may be interlocked with handling of the hand release switch or foot switch. Alternatively, one switch may be used exclusively. In this case, a switch signal is controlled by the CPU 338 and control unit 345, so that image data will be recorded on the external recording device 310 such as a PC card after it is confirmed that the image data has been written in the memory 342 in the digital interface unit 309.

A digital video signal sent from the DSP 335 is output to the digital output circuit 339 under the control of the CPU 338. The digital video signal is thus output to the digital interface unit 309 via the digital output circuit 339.

During a write operation, a vertical sync signal (V-SYNC), a horizontal sync signal (H-SYNC), a field signal (even/odd), a vertical blanking signal (V-BLNK), and a clock signal (CLK) and horizontal blanking signal (H-BLNK) which are illustrated in enlargement relative to one pulse of the horizontal sync signal are input to the memory control signal generator 344 in the digital interface unit 309. The clock signal (CLK) is also input to the control unit 345. The control signal 345 controls the memory control signal generator 344 synchronously with the clock signal (CLK) in response to the clock signal (CLK) and an ON signal sent from the switch 346 included in the digital interface unit 309. This causes the memory control signal generator 344 to output a memory control signal that is a write signal to the memory 342. The digital video signal is then stored in the memory 342.

During a read operation, an address signal and control signal sent from the external recording device 310 are input to the memory control generator 344. The control signal is input to the control unit 345. The control unit 345 controls the memory control signal generator 344 according to the control signal. This causes the memory control signal generator 344 to output a memory control signal that is a read signal to the memory 342. The digital video signal is then read from the memory 342, and output to the external recording device 310 via the data output interface 343.

Thus, the read and write operations to be performed on a digital video signal relative to the memory 342 are controlled with a memory control signal generated by the memory control signal generator 344 controlled by the control unit 345. This embodiment provides advantages described below.

As mentioned above, the endoscopic imaging system 301 of this embodiment has the memory 342, in which image data is stored, included in the digital interface unit 309. A digital video signal stored in the memory 342 can be read according to an address signal and control signal sent from the external recording device 310. This obviates the necessity of providing an image memory for the external recording device 310. Moreover, the digital video signal in the memory 342 can be read merely by designating an address. Thus, image data can be stored or recorded readily.

Figure 18:
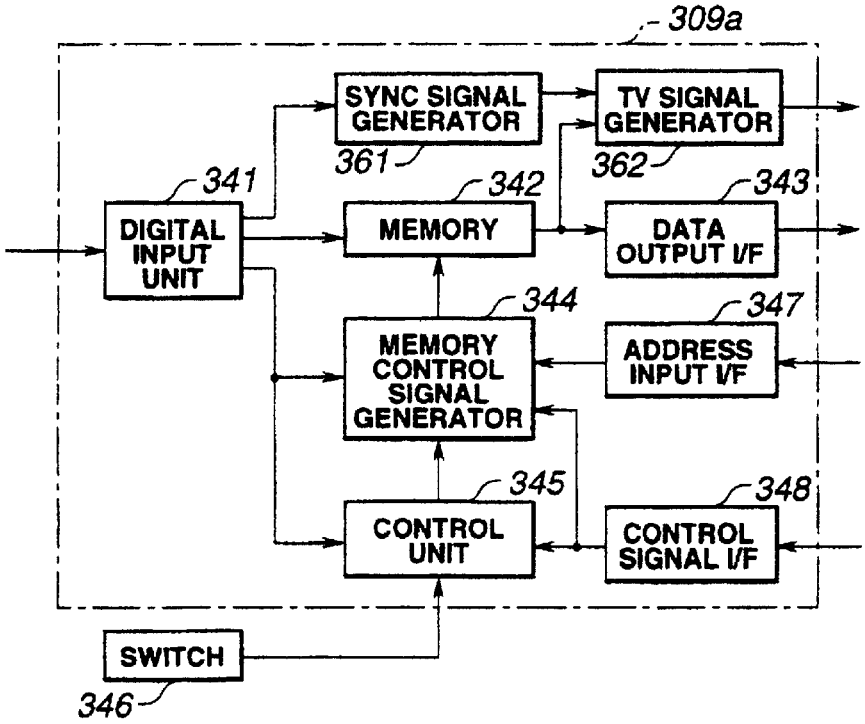
FIG. 18 is a diagram showing a configuration of a digital interface unit in accordance with a seventh embodiment of the present invention.

FIG. 18 shows a configuration of a digital interface unit in a seventh embodiment of the present invention. The seventh embodiment is nearly identical to the sixth embodiment. Only the difference will be described below. The same reference numerals will be assigned to the components which are the same as in the sixth embodiment. The description of those the components will therefore be omitted.

A digital interface unit 309a in this embodiment comprises, as shown in FIG. 18, a sync signal generator 361 for receiving as input a clock signal (CLK), horizontal sync signal, and vertical sync signal, which are input together with a digital video signal sent from the DSP 335, via digital output circuit 339 to generate a sync signal, and a TV signal generator 362 for receiving input the digital video signal that has been stored in the memory 342 and read according to an address signal and control signal sent from the external recording device 310, and generating a standard TV signal synchronously with a sync signal generated by the sync signal generator 361.

The other components are identical to those of the sixth embodiment. Next, the operations of this embodiment will be described.

In this embodiment, like the sixth embodiment, an address signal and control signal sent from the external recording device 310 are input to the address input interface 347 and control signal interface 348. The control signal sent from the control signal interface 348 is input to the control unit 345.

The control unit 345 controls the memory control signal generator 344 according to the control signal. This causes the memory control signal generator 344 to output a memory control signal that is a read signal to the memory 342 and read a digital video signal from the memory 342. The digital video signal is output to the external recording device 310 via the data output interface 343.

At this time, the sync signal generator 361 generates a sync signal using a clock signal (CLK), horizontal sync signal, and vertical sync signal which are input together with a digital video signal sent from the DSP 335. The TV signal generator 362 inputs the digital video signal that has been stored in the memory 342 and read according to an address signal and control signal sent from the memory control signal generator 344. The TV signal generator 362 then generates a standard TV signal according to the sync signal generated by the sync signal generator 361. An image whose data is output to the external recording device 310 is checked on the monitor that is not shown.

Except when data is recorded on the external recording device 310 (when no input signal is sent from the external recording device 310 to the control signal interface 348 and address input interface 347), data is read from the memory 342 according to the clock signal (CLK). When an input signal is sent, data is read according to signals sent from the control signal interface 348 and address input interface 347. The other operations are identical to those of the sixth embodiment. This embodiment provides advantages described below.

This embodiment can provide the same advantage as the sixth embodiment. Additionally, since image data represented by a digital video signal output to the external recording device 310 is output to the monitor by the TV signal generator 362, an image represented by the image data can be checked readily. After it is confirmed that the image is a desired image, the digital video signal can be recorded on the external recording device 310.

Figure 19:
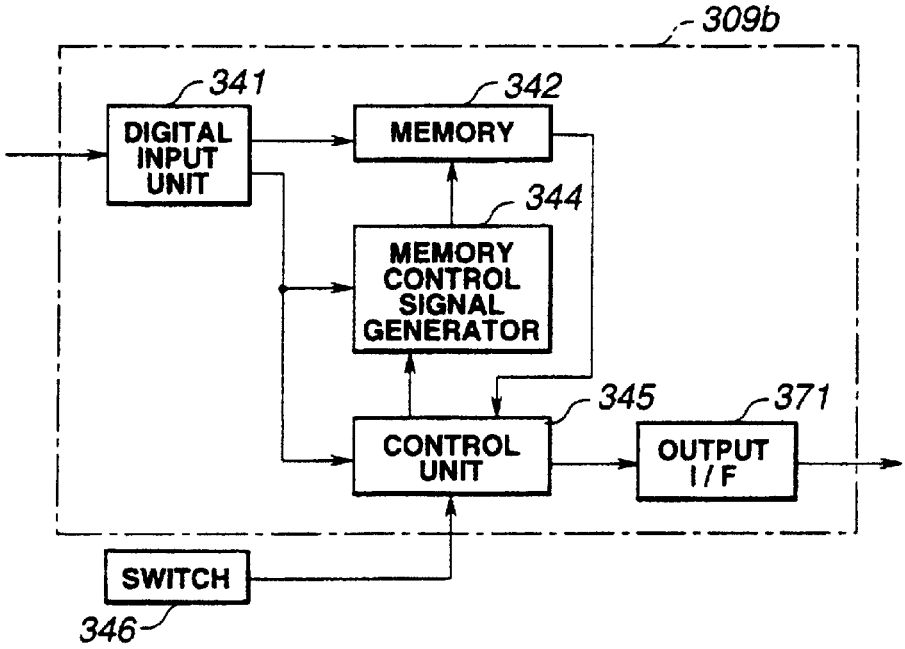
FIG. 19 is a diagram showing a configuration of a digital interface unit in accordance with a eighth embodiment of the present invention.

FIG. 19 shows a configuration of a digital interface unit in an eighth embodiment of the present invention.

The eighth embodiment is nearly identical to the sixth embodiment. Only the difference will be described below. The same reference numerals will be assigned to the same components. The description of those components will therefore be omitted.

In the sixth embodiment, a digital video signal stored in the memory 342 is read according to an address signal and control signal sent from the external recording device 310. In this embodiment, a digital interface unit 309b includes the external recording device 310 and an output interface 371 capable of carrying out serial data transmission according to the RS-232C in place of the address input interface 347, control signal interface 348, and data output interface 343. Incidentally, the output interface 371 may be an SCSI interface.

The other components are identical to those of the sixth embodiment. Next, the operations of the eight embodiment will be described.

In this embodiment, the control unit 345 communicates with the external recording device 310 via the output interface 371 during a read operation. The control unit 345 reads a digital video signal stored in the memory 342 in response to a command sent from the external recording device 310, and outputs the digital video signal to the external recording device 310 via the output interface 371. The other operations are identical to those of the sixth embodiment. This embodiment provides an advantage described below.

In this embodiment, as mentioned above, the control unit 345 communicates with the external recording device 310 via the output interface 371. A digital video signal stored in the memory 342 is read under the control of the control unit 345. Even when the external recording device 310 is slow at fetching data, a digital video signal stored in the memory 342 can be fetched reliably under the control of the control unit 345.

Figure 20:
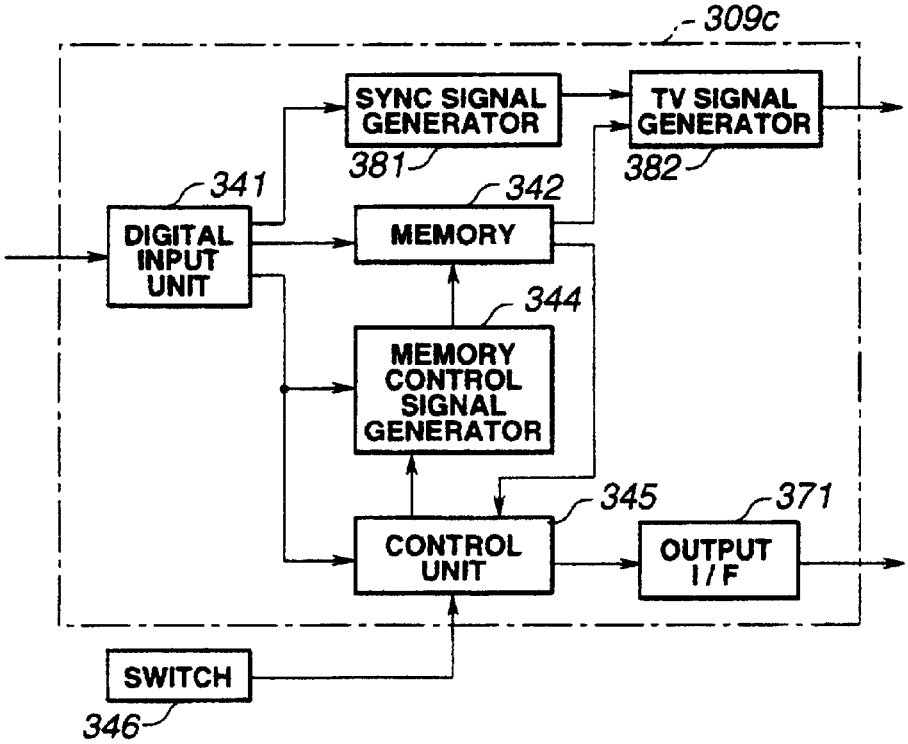
FIG. 20 is a diagram showing a configuration of a digital interface unit in accordance with a ninth embodiment of the present invention.

FIG. 20 shows a configuration of a digital interface unit in a ninth embodiment of the present invention.

The ninth embodiment is nearly identical to the eighth embodiment. Only the difference will be described. The same reference numerals will be assigned to the same components. The description of those components will thus be omitted.

According to this embodiment, as shown in FIG. 20, a digital interface unit 309c comprises a sync signal generator 381 for receiving a clock signal (CLK) that is input together with a digital video signal sent from the DSP 335, and for generating a sync signal, and a TV signal generator 382 for receiving a digital video signal that has been stored in the memory 342 and read according to an address signal and control signal sent from the external recording device 310, and for generating a standard TV signal synchronous with a sync signal generated by the sync signal generator 381.

The other components are identical to those of the sixth embodiment. Next, the operations of the ninth embodiment will be described.

In this embodiment, like the eighth embodiment, the control unit 345 communicates with the external recording device 310 via the output interface 371 during a read operation. The control unit 345 reads a digital video signal stored in the memory 342 in response to a command sent from the external recording device 310, and outputs the digital video signal to the external recording device 310 via the output interface 371.

At this time, the sync signal generator 381 receives a clock signal (CLK) that is input together with a digital video signal sent from the DSP 335, and generates a sync signal. The TV signal generator 382 receives a digital video signal that has been stored in the memory 342 and read according to an address signal and control signal sent from the memory control signal generator 344, and generates a standard TV signal synchronously with a sync signal generated by the sync signal generator 381. An image whose data is output to the external recording device 310 can be checked on a monitor that is not shown.

The other operations are identical to those of the sixth embodiment. This embodiment provides advantages described below.

This embodiment provides the same advantage as the eighth embodiment. Additionally, image data represented by a digital video signal to be output to the external recording device 310 is output to the monitor by the TV signal generator 382. An image represented by the image data can be checked readily. After it is confirmed that the image is a desired image, the digital video signal can be recorded on the external recording device 310.

Figure 21:
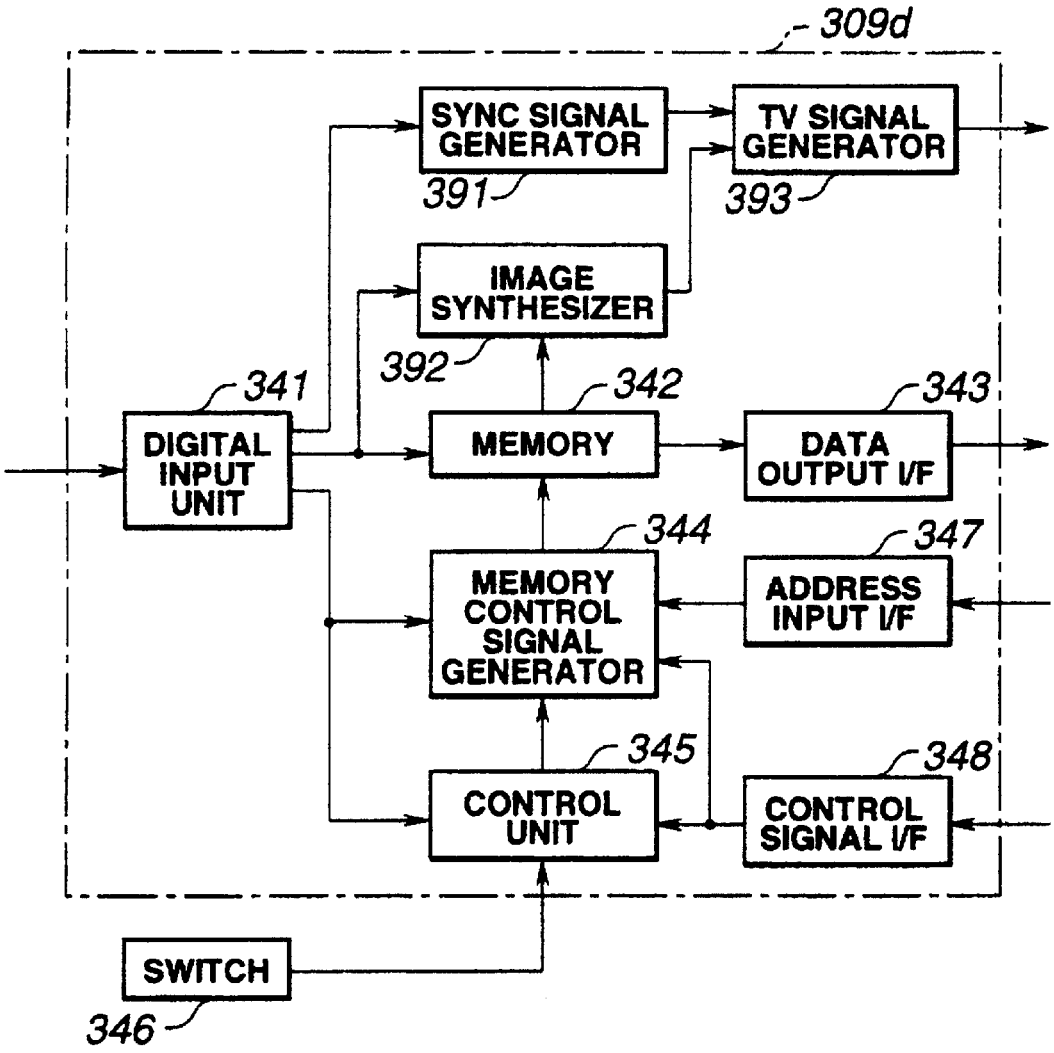
FIG. 21 is a diagram showing a configuration of a digital interface unit in accordance with a tenth embodiment of the present invention.

FIG. 21 shows a configuration of a digital interface unit in a tenth embodiment of the present invention.

The tenth embodiment is nearly identical to the sixth embodiment. Only the difference will be described below. The same reference numerals will be assigned to the same components. The description of those components will thus be omitted.

According to this embodiment, as shown in FIG. 21, a digital interface unit 309d comprises a sync signal generator 391 for receiving a clock signal (CLK) that is input together with a digital video signal sent from the DSP 335 and generating a sync signal, for an image synthesizer 392 for receiving a digital video signal that has been stored in the memory 342 and read according to an address signal and control signal sent from the external recording device 310 and a current digital video signal input from the digital input unit 341, and for synthesizing the digital video signal stored in the memory 342 with the current digital video signal input from the digital input unit 341 so as to generate synthetic image data in a picture-in-picture form, and a TV signal generator 393 for receiving the synthetic image data generated by the image synthesizer 392 and generating a standard TV signal synchronously with the sync signal generated by the sync signal generator 391.

The other components are identical to those of the sixth embodiment. Next, the operations of the tenth embodiment will be described.

In this embodiment, like the sixth embodiment, an address signal and control signal sent from the external recording device 310 are input to the address input interface 347 and control signal interface 348 during a read operation. The address signal and control signal sent from the address input interface 347 and control signal interface 348 are input to the memory control signal generator 344. The control signal sent from the control signal interface 348 is also input to the control unit 345.

The control unit 345 controls the memory control signal generator 344 according to the control signal. This causes the memory control signal generator 344 to output a memory control signal that is a read signal to the memory 342. A digital video signal is read from the memory 342 and output to the external recording device 310 via the data output interface 343.

At this time, the sync signal generator 391 receives a clock signal (CLK) that is input together with a digital video signal sent from the DSP 335 and generates a sync signal. The image synthesizer 392 synthesizes a digital video signal stored in the memory 342 with a current digital video signal input from the digital input unit 341 so as to generate synthetic image data in a picture-in-picture form. The TV signal generator 393 receives the synthetic image data generated by the image synthesizer 392 and generates a standard TV signal synchronously with the sync signal generated by the sync signal generator 391. Consequently, the synthetic image having the image whose data is output to the external recording device 310 inlet in the picture-in-picture form can be checked on a monitor that is not shown.

The other operations are identical to those of the sixth embodiment.

As mentioned above, this embodiment provides the same advantage as the sixth embodiment. Additionally, synthetic image data having image data, which is represented by a digital video signal to be output to the external recording device 310, inlet in the picture-in-picture form can be output to a monitor by the TV signal generator 393. An image represented by the digital video signal to be output to the external recording device 310 can be checked readily. After it is confirmed that the image is a desired image, the digital video signal can be recorded on the external recording device 310.

The sixth to tenth embodiments have been described with reference to the TV camera-mounted endoscope 304 having the TV camera 303 mounted on the rigid endoscope 302 as an example. The present invention is not limited to this type of endoscope. A TV camera-mounted soft endoscope having the TV camera 303 mounted on a soft endoscope or an electronic endoscope having a CCD incorporated in the distal part of an insertion unit thereof may also be used in accordance with the present invention.

As described so far, according to the endoscopic imaging systems of the sixth to tenth embodiments, a storage means stores a digital signal, and a control means controls the storage means. This brings about the advantages that an external storage has a simple structure and that digital image data can be fetched readily.

Incidentally, further embodiments to be constructed by combining parts of the aforesaid embodiments will belong to the present invention.

What is claimed is:

1. An endoscopic imaging system, comprising:

an endoscope including an elongated insertion unit having a terminal portion, an illumination optical system located at the terminal portion of the elongated insertion unit for emitting illumination light, an objective optical system located at the terminal portion of said insertion unit for forming an optical image of an object illuminated with the illumination light, and an imaging device for photoelectrically converting the optical image either directly upon formation or after being transmitted through the insertion unit;

a signal processing apparatus for driving said imaging device, processing an image signal output from said imaging device, generating a digital video signal and an analog video signal, and outputting the video signals through a digital video signal output terminal and analog video signal output terminal, respectively;

a monitor for displaying an object image represented by the analog video signal in response to input of the analog video signal output through said analog video signal output terminal; and an expansion unit to be coupled to said digital video signal output terminal in a freely detachable manner, the expansion unit being provided with at least one of a compression unit for compressing data represented by the digital video signal and a PC card slot to which a PC card on which a digital video signal representing a still image whose data has been compressed by said compression unit is stored can be coupled in the freely detachable manner.

2. An endoscopic imaging system according to claim 1, wherein said PC card is a small memory card selected from the group consisting of a smart medium, a compact flash memory card, [A] *a* miniature card, a small PC card, an adapter card to be coupled to said PC card slot in a freely detachable manner with a small memory card freely detachably attached thereto, and a hard disk of type III.

3. An endoscopic imaging system according to claim 1, wherein said digital video signal output terminal is used to provide an output signal conformable to the IEEE 1394 standard.

4. An endoscopic imaging system according to claim 1, wherein said signal processing apparatus includes a communication line over which a control signal is transmitted to said expansion unit.

5. An endoscopic imaging system according to claim 1, wherein said signal processing apparatus includes a display [elements] *element* for displaying a number of still images that have been recorded using said expansion unit.

6. An endoscopic imaging system according to claim 4, wherein said communication line has the ability to transmit information sent from said expansion unit, and the transmitted information is displayed during said signal processing.

7. An endoscopic imaging system according to claim 1, wherein said endoscope is an electronic endoscope having said imaging device located at an image formation position of said objective optical system.

8. An endoscopic imaging system according to claim 1, wherein said endoscope is an optical endoscope including an image transmitter for transmitting an optical image formed by said objective optical system, in which said imaging device is incorporated or mounted on said optical endoscope in a freely detachable manner.

9. An endoscopic image system according to claim 1, wherein said signal processing apparatus includes a frame memory into which the digital video signal is written temporarily, such that when the digital video signal *is* read from said frame memory, the digital video signal is output through said digital video signal output terminal.

10. An endoscopic imaging system according to claim 1, wherein said expansion unit is a still image-specific expansion unit including said compression unit and said PC card slot.

11. An endoscopic imaging system according to claim 1, wherein said expansion unit is a motion picture-specific expansion unit including said compression unit and a motion picture digital video signal output terminal.

12. An endoscopic imaging system according to claim 1, wherein said expansion unit is a still image and motion picture-specific expansion unit including said compression unit, said PC card slot, and a motion picture digital video signal output terminal.

13. An endoscopic imaging system according to claim 1, further comprising an identification unit for recognizing an expansion unit coupled to said digital video signal output terminal as either a motion picture-specific expansion unit or a still image-specific expansion unit.

14. An endoscopic imaging system according to claim 13, further comprising a release switch, wherein when said release switch is handled, said signal processing apparatus outputs either image data of a still image to said still image-specific expansion unit or image data of a motion picture to said motion picture-specific expansion unit through said digital video signal output terminal according to the result of the recognition process performed by said identification unit.

15. An endoscopic imaging system according to claim 10, wherein said still image-specific expansion unit further includes a first compression unit of a lossless coding type and a second compression unit of a lossy coding type, and an instruction element for instructing which of said first compression unit and said second compression unit should be selected for recording a still image.

16. An endoscopic imaging system according to claim 1, wherein said signal processing apparatus has a digital video output terminal to which a still image-specific expansion unit and motion picture-specific expansion unit can be coupled simultaneously.

17. An endoscopic imaging system according to claim 1, further comprising a recording [elements] *element* for transferring and recording image data to be recorded on said PC card.

18. An endoscopic imaging system according to claim 1, further comprising a recording element for recording image data of a compressed still image on a medium other than a PC card loaded into said expansion unit.

19. An endoscopic imaging system according to claim 1, wherein a connection between said digital video signal output terminal and an input terminal of said expansion unit is configured to provide ground-level voltage, power, and data connections in the listed order.

20. An endoscopic image system according to claim [19] *1*, wherein when power is supplied from a unit other than said signal processing apparatus to said expansion unit, a connection between said digital video signal output terminal *and an input terminal of said expansion unit* is configured to provide the ground-level voltage and data connections in the listed order.

21. An endoscopic imaging system according to claim 19, wherein the connection between said digital video signal output terminal and said input terminal of said expansion unit is established through pins, and wherein the length of a ground pin is the longest and the length of a power pin is shorter than the length of the ground pin and longer than the length of a data transfer pin.

22. An endoscopic imaging system according to claim 20, wherein the connection between said digital video signal output terminal and said input terminal of said expansion unit is established through pins, and wherein the length of a ground pin is longest of all the pins, and the length of a data transfer pin is shorter than the length of any other type of pin.

23. An endoscopic imaging system according to claim 1, further comprising a plurality of contact points for a ground line, a power line, and a data line, respectively, which are enclosed in a bus at said digital video signal output terminal and which are positioned such that the ground line will come into contact with said expansion unit first, the power line will come into contact therewith second, and the data line will come into contact therewith last when said bus is connected to said expansion unit.

24. An endoscopic imaging system, comprising:

an endoscope including an elongated insertion unit having a terminal portion, an illumination optical system located at the terminal portion of the elongated insertion unit for emitting illumination light, an objective optical system located at the terminal portion of said insertion unit for forming an optical image of an object illuminated with the illumination light, and an imaging device for photoelectrically converting the optical image either directly upon formation or after being transmitted through the insertion unit;

a signal processing apparatus for driving said imaging device, processing an image signal output from said imaging device, producing a digital video signal and an analog video signal, and outputting the video signals through a digital video signal output terminal and analog video signal output terminal, respectively;

a monitor for displaying an object image represented by the analog video signal in response to input of the analog video signal output through said analog video signal output terminal;

a digital interface unit to be coupled to said digital video signal output terminal in a freely detachable manner, the digital interface unit including a memory in which said digital video signal is stored temporarily, a controller for controlling a read operation and a write operation to be performed relative to said memory, and a digital interface output unit for outputting the digital video signal upon being read from said memory in a form acceptable by an external device; and an external storage/recording device coupled to said digital video output terminal for storing or recording said digital video signal.

25. An endoscopic imaging system according to claim 24, wherein said controller is incorporated in said digital interface unit.

26. An endoscopic imaging system according to claim 24, further comprising a video signal generator for generating a video signal using said digital video signal stored in said memory.

27. An endoscopic imaging system according to claim 24, further comprising an image synthesizer for synthesizing said digital video signal produced by said signal processing apparatus and said digital video signal stored in said memory, so as to produce synthetic image data; and a synthetic video signal generator for generating a video signal using the synthetic image data produced by said image synthesizer.

*28. An endoscopic image system according to claim 1, further comprising a light source unit of a surface sequential type which includes a white light source which emits white light, and a rotary filter which rotates to recompose the white light into sequential light rays of red, green and blue.*

*29. An image processing system for an endoscopic imaging system, comprising:*

*a signal processing apparatus for driving an imaging device of a type which photoelectrically converts an optical image into an image signal, processing an image signal output from said imaging device, generating a digital video signal and an analog video signal, and outputting the video signals through a digital video signal output terminal and analog video signal output terminal, respectively; and*

*an expansion unit to be connected to said digital video signal output terminal in a freely detachable manner, the expans~0n unit being provided with at least one of a compression unit for compressing data represented by the digital video signal, at least one PC card slot to which a PC card for storing digital video signal data which has been compressed by said compression unit and which represents a still image can be coupled in a freely detachable manner, and a motion picture digital video signal output terminal.*

*30. An image processing system according to claim 29, wherein said signal processing apparatus includes a display element for displaying a number of still images that have been recorded or a time length of a motion picture that has been recorded using said expansion unit.*

*31. An image processing system according to claim 29, wherein the digital video signal is transferred to said expansion unit in a parallel transfer mode.*

*32. An image processing system according to claim 29, wherein the digital video signal is transferred to said expansion unit in a serial transfer mode.*

*33. An image processing system according to claim 29, wherein said expansion unit is a still image-specific expansion unit including said compression unit and said at least one PC card slot.*

*34. An image processing system according to claim 33, wherein said signal processing apparatus includes a modem whereby said signal processing apparatus is capable of transferring digital video signal data to an external medium while a PC card is loaded in said PC card slot.*

*35. An image processing system according to claim 33, wherein said compression unit compresses said data according to a lossy coding.*

*36. An image processing system according to claim 33, wherein said compression unit compresses said data according to a lossless coding.*

*37. An image processing system according to claim 33, further comprising a recording element for recording image data of a compressed still image on a medium other than a PC card loaded into said expansion unit.*

*38. An image processing system according to claim 37, wherein said recording element can be detachably coupled to said expansion unit.*

*39. An image processing system according to claim 29, wherein said expansion unit is a motion picture-specific expansion unit including said compression unit and said motion picture digital video signal output terminal.*

*40. An image processing system according to claim 29, wherein said expansion unit is a still image and motion picture-specific expansion unit including said compression unit, said at least one PC card slot, and a motion picture digital video signal output terminal.*

*41. An image processing system according to claim 29, wherein said signal processing apparatus is configured to recognize an expansion unit connected to said digital video signal output terminal and identify the same as either a motion picture-specific expansion unit or a still image-specific expansion unit.*

*42. An image processing system according to claim 41, further comprising a release switch operable by a user to cause said signal processing apparatus to output either image data of a still image to said still image-specific expansion unit or image data of a motion picture to said motion picture-specific expansion unit through said digital video signal output terminal according to a recognition by said signal processing apparatus of said expansion unit connected thereto.*

*43. An image processing system according to claim 29, wherein said signal processing apparatus has two digital video output terminals so that both of a still image-specific expansion unit and a motion picture-specific expansion unit can be coupled to said signal processing apparatus simultaneously.*

*44. An image processing system according to claim 29, further comprising a frame memory incorporated in one of said signal processing apparatus or said expansion unit for temporarily storing digital video signal data to facilitate recording of said data via said expansion unit.*

*45. An image processing system according to claim 29, further comprising a connection interface between said digital video signal output terminal of said signal processing apparatus and said expansion unit, said interface including a plurality of contact elements for a ground line, a power line, and a data line, respectively, which are positioned such that the ground line will come into contact with said expansion unit first, the power line will come into contact therewith second, and the data line will come into contact therewith last when said bus is connected to said expansion unit.*

*46. An image processing system according to claim 29, further comprising a connection interface between said digital video signal output terminal of said signal processing apparatus and said expansion unit, said interface including a plurality of contact elements for a ground line and a data line, respectively, which are positioned such that the ground line will come into contact with said expansion unit first and the data line will come into contact therewith last when said bus is connected to said expansion unit.*

*47. An image processing system according to claim 46, wherein said connection interface further comprises a control signal line over which a control signal is transmitted in parallel to data transmission over said data line.*

*48. An image processing system according to claim 46, wherein said connection interface further comprises two control signal lines for bi-directional transmission of control signals in parallel to data transmission over said data line.*

*49. An image processing system according to claim 29, further comprising a digital interface unit to be coupled in a freely detachable manner between said digital video signal output terminal of said signal processing apparatus and said expansion unit, the digital interface unit including*

*a memory in which said digital video signal is stored temporarily,*

*a controller for controlling a read operation and a write operation to be performed relative to said memory, and*

*a digital interface output unit for outputting, upon being read from said memory, the digital video signal in a form acceptable to said expansion unit.*

*50. An image processing system according to claim 49, wherein said digital interface unit further includes a video signal generator for generating a video signal using said digital video signal stored in said memory.*

*51. An image processing system according to claim 49, wherein said digital interface unit further includes an image synthesizer for synthesizing said digital video signal produced by said signal processing apparatus and said digital video signal stored in said memory, so as to produce synthesized image data; and a synthetic video signal generator for generating a video signal using the synthesized image data produced by said image synthesizer.*

*52. An image processing system according to claim 29, wherein said PC card is a small memory card selected from the group consisting of a smart medium, a compact flash memory card, a miniature card, a small PC card, an adapter card to be coupled to said PC card slot in a freely detachable manner with a small memory card freely detachably attached thereto, and a hard disk of type III.*

* * * * *